United States Patent
Hirakawa

(10) Patent No.: US 8,419,619 B2
(45) Date of Patent: Apr. 16, 2013

(54) ENDOSCOPIC FORM DETECTION DEVICE AND FORM DETECTING METHOD OF INSERTION SECTION OF ENDOSCOPE

(75) Inventor: Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 87 days.

(21) Appl. No.: 13/229,182

(22) Filed: Sep. 9, 2011

(65) Prior Publication Data
US 2012/0053418 A1    Mar. 1, 2012

Related U.S. Application Data

(63) Continuation of application No. PCT/JP2011/059637, filed on Apr. 19, 2011.

(30) Foreign Application Priority Data

May 31, 2010  (JP) .................................. 2010-125154

(51) Int. Cl.
| | |
|---|---|
| A61B 1/00 | (2006.01) |
| A61B 1/04 | (2006.01) |
| A61B 5/05 | (2006.01) |
| G01P 15/00 | (2006.01) |

(52) U.S. Cl.
USPC .............. 600/117; 600/424; 600/145; 73/488

(58) Field of Classification Search .................. 600/117, 600/101, 424, 145, 146, 434; 33/503; 73/488
See application file for complete search history.

(56) References Cited

U.S. PATENT DOCUMENTS

| 6,059,718 | A  * | 5/2000  | Taniguchi et al. | 600/117 |
|---|---|---|---|---|
| 7,296,363 | B2 * | 11/2007 | Danisch et al. | 33/556 |
| 7,691,056 | B2 * | 4/2010  | Hirata | 600/129 |
| 2004/0116775 | A1 * | 6/2004 | Taniguchi et al. | 600/117 |

(Continued)

FOREIGN PATENT DOCUMENTS

| JP | A-11-19027 | 1/1999 |
|---|---|---|
| JP | A-2000-175862 | 6/2000 |

(Continued)

OTHER PUBLICATIONS

International Search Report issued in International Application No. PCT/JP2011/059637 dated May 31, 2011 (with translation).
Office Action issued in Japanese Patent Application No. 2011-535736 dated Oct. 25, 2011 (with translation).

*Primary Examiner* — John P Leubecker
*Assistant Examiner* — Ronald D Colque
(74) *Attorney, Agent, or Firm* — Oliff & Berridge, PLC

(57) ABSTRACT

An endoscopic form detection device includes a posture detecting section configured to detect a posture of each of sensor units based on measurement data in the sensor unit, and a linear form detecting section configured to detect a detected linear form of an inserting section on an assumption that a form between the respective sensor units is a linear link whose dimension is equal to an inter-sensor dimension based on the detected posture of each of the sensor units. The endoscopic form detection device includes a curve form detecting section configured to perform curve interpolation with respect to the detected linear form detected on an assumption that a form between the respective sensor units is an arc whose arc length is equal to the inter-sensor dimension, and configured to detect a detected curve form.

12 Claims, 13 Drawing Sheets

U.S. PATENT DOCUMENTS

| | | | |
|---|---|---|---|
| 2005/0284221 A1* | 12/2005 | Danisch et al. | 73/488 |
| 2006/0173289 A1* | 8/2006 | Aizawa et al. | 600/424 |
| 2007/0106114 A1* | 5/2007 | Sugimoto et al. | 600/117 |
| 2007/0106116 A1* | 5/2007 | Sugimoto | 600/117 |
| 2007/0112247 A1* | 5/2007 | Hirata | 600/101 |
| 2010/0191056 A1* | 7/2010 | Tanaka | 600/117 |
| 2010/0204545 A1* | 8/2010 | Tanaka et al. | 600/109 |

FOREIGN PATENT DOCUMENTS

| | | |
|---|---|---|
| JP | A-2007-130154 | 5/2007 |
| JP | A-2007-319622 | 12/2007 |
| JP | A-2010-104426 | 5/2010 |

* cited by examiner

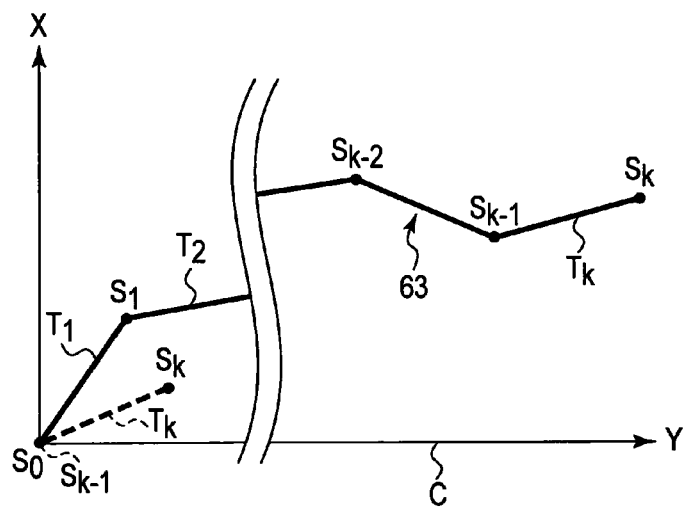
F I G. 7
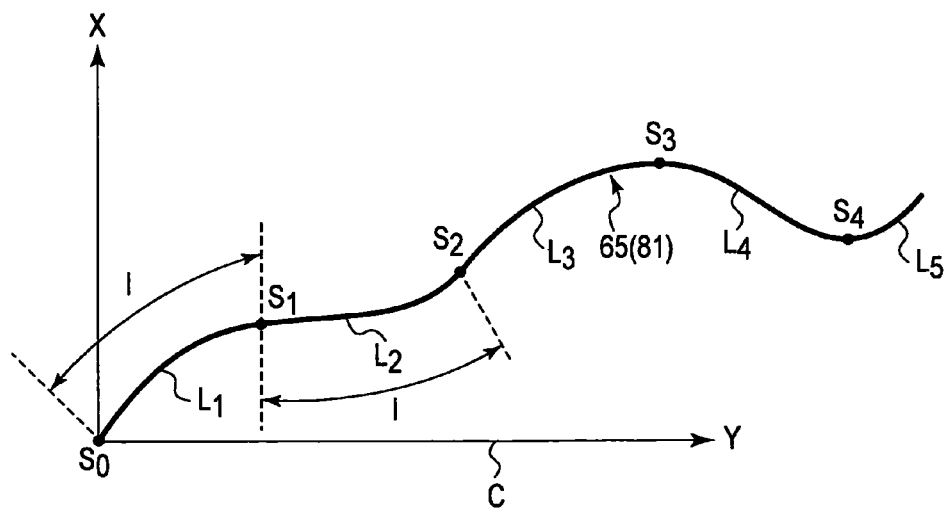
F I G. 8

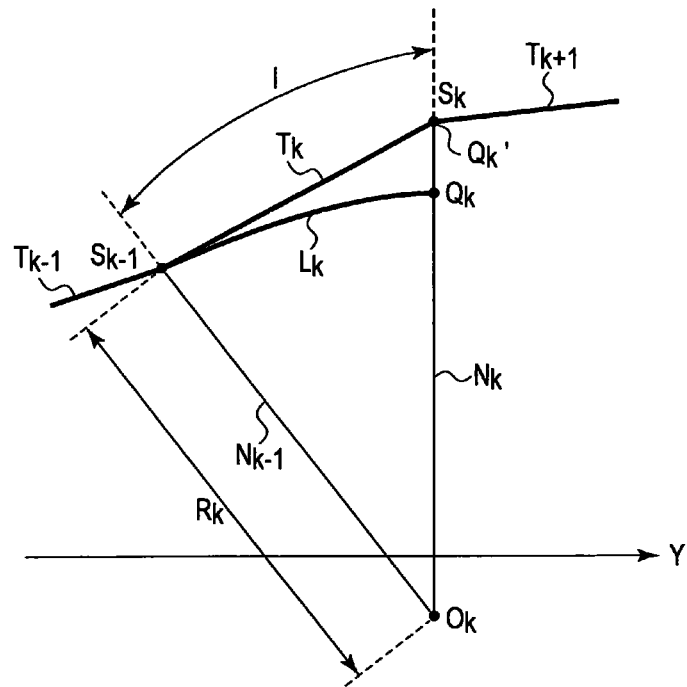
F I G. 10
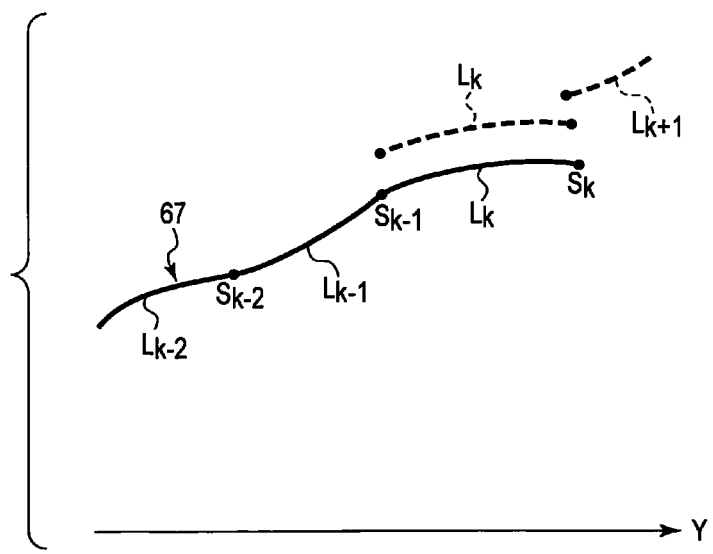
F I G. 11

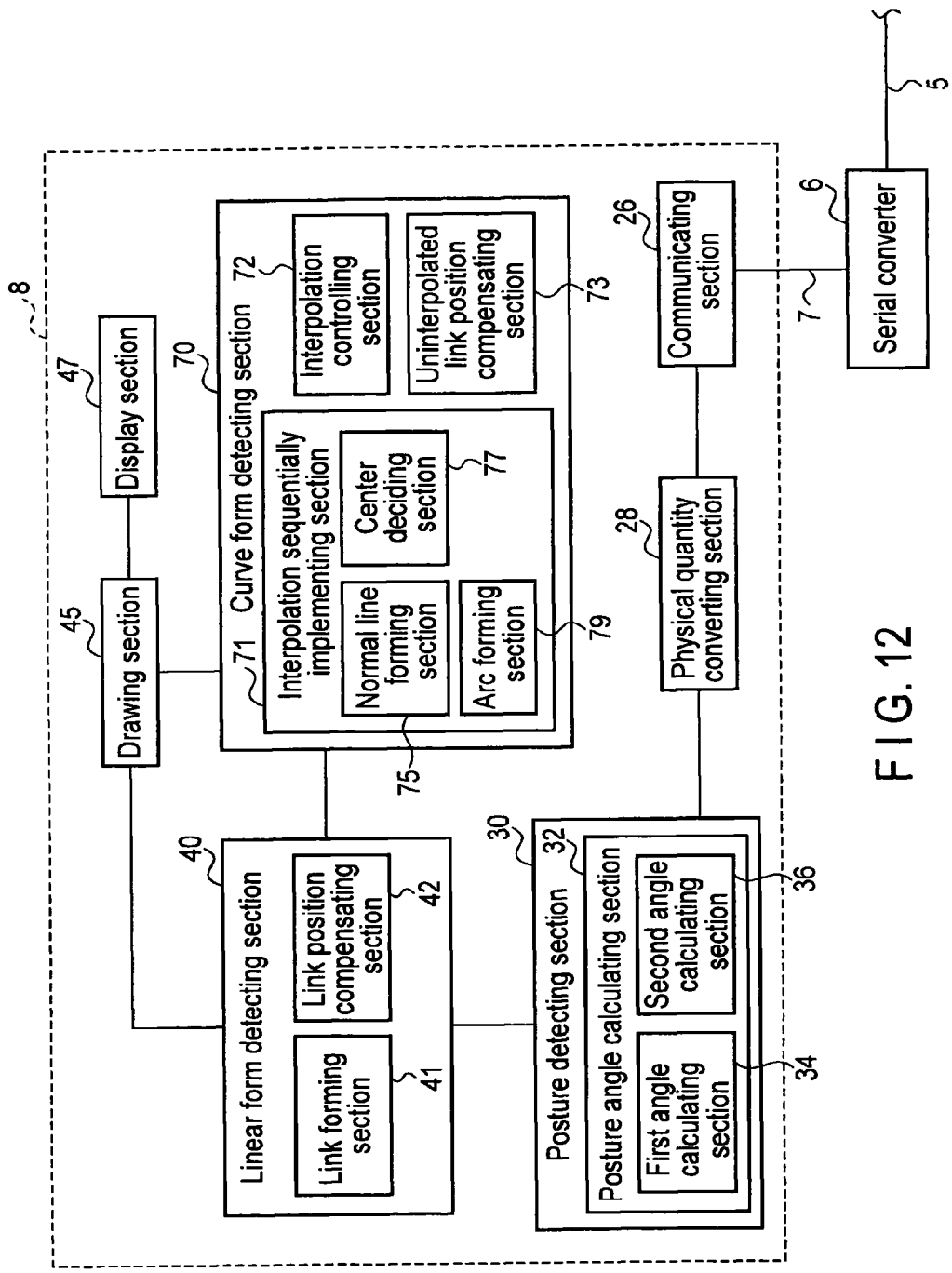
F I G. 12

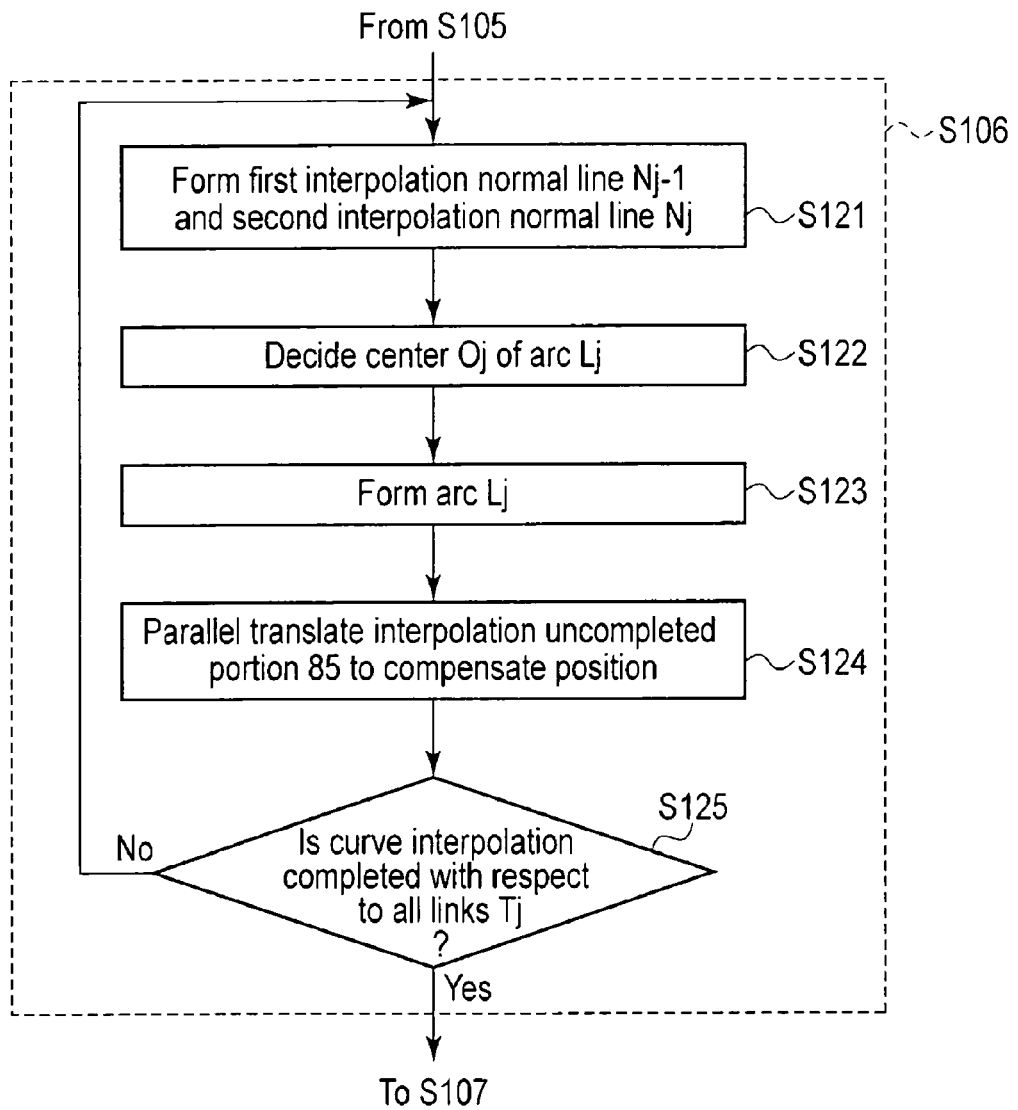
F I G. 13

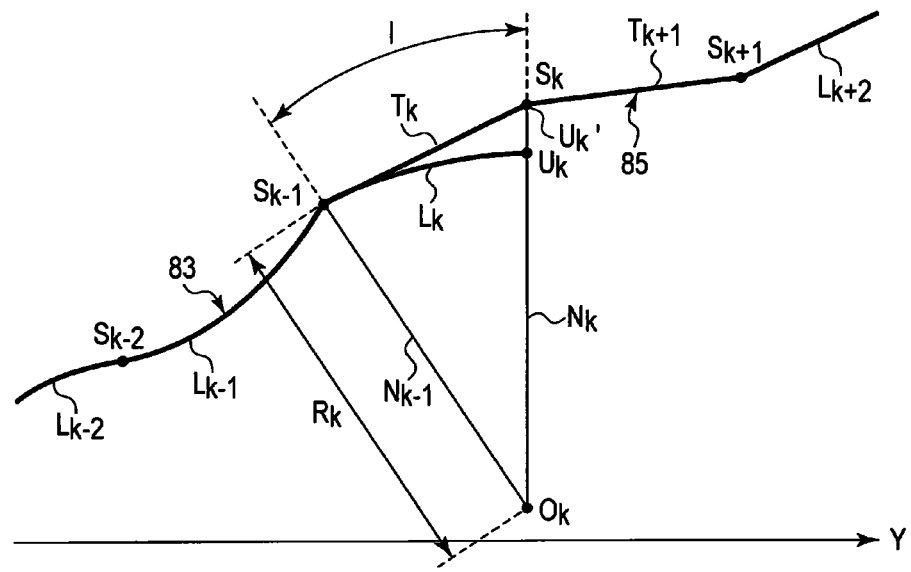
F I G. 14
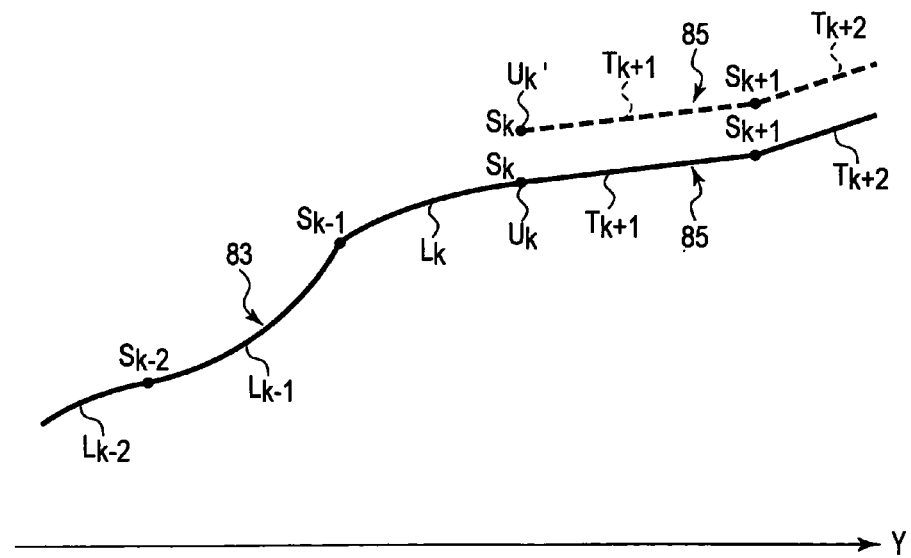
F I G. 15

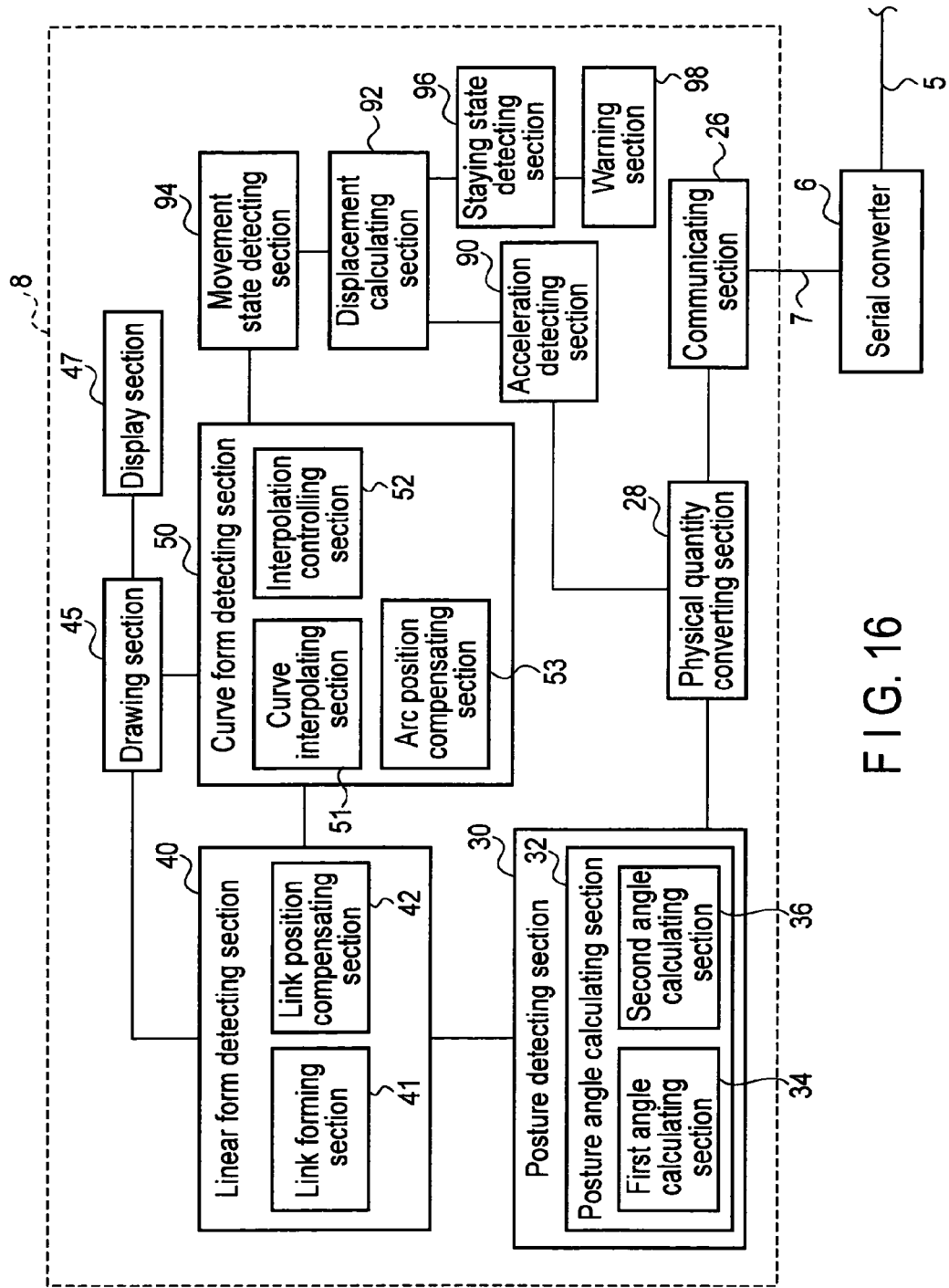
F I G. 16

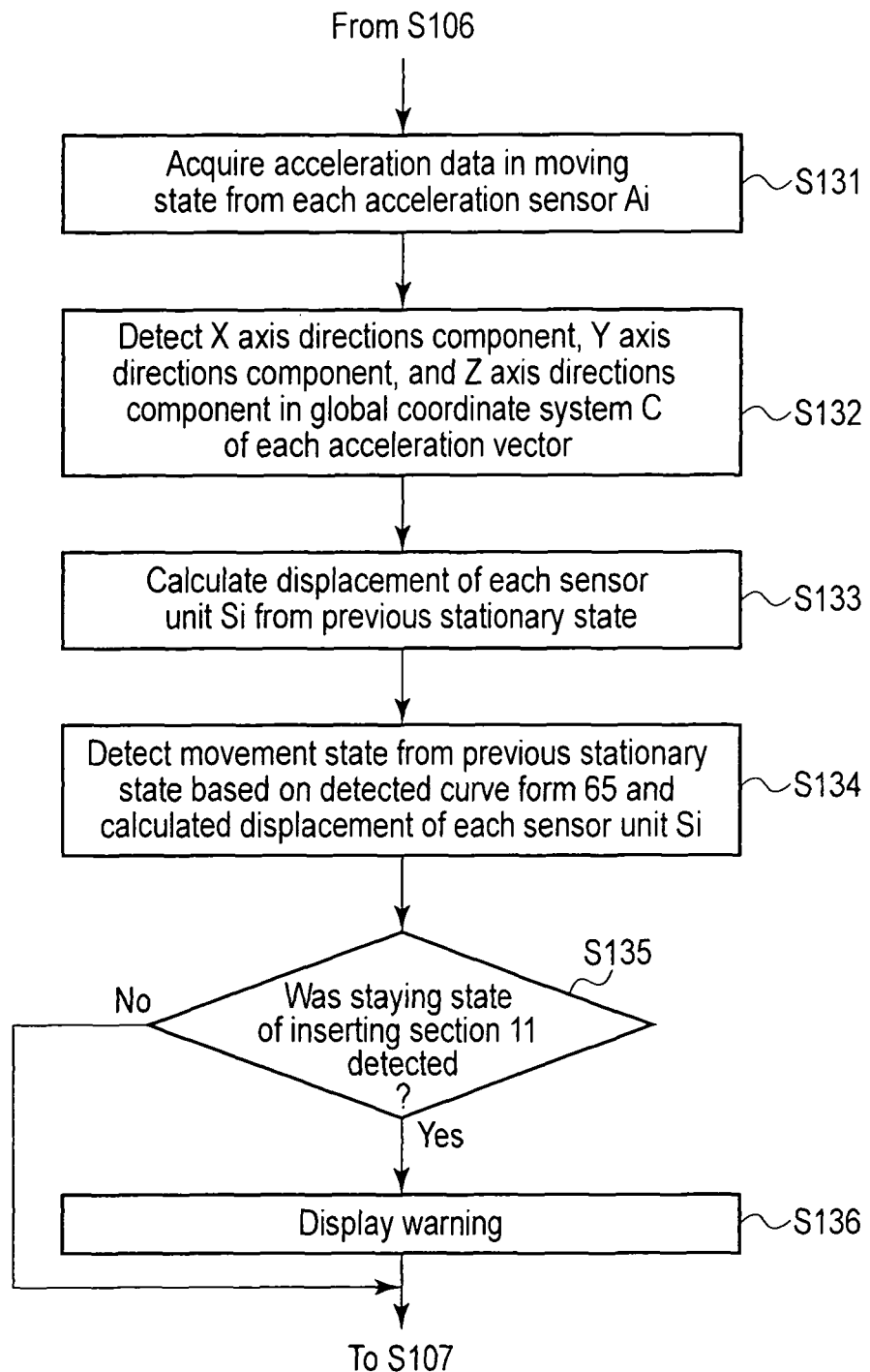
F I G. 17

ENDOSCOPIC FORM DETECTION DEVICE AND FORM DETECTING METHOD OF INSERTION SECTION OF ENDOSCOPE

CROSS REFERENCE TO RELATED APPLICATIONS

This application is a Continuation Application of PCT Application No. PCT/JP2011/059637, filed Apr. 19, 2011 and based upon and claiming the benefit of priority from prior Japanese Patent Application No. 2010-125154, filed May 31, 2010, the entire contents of all of which are incorporated herein by reference.

BACKGROUND OF THE INVENTION

1. Field of the Invention

The present invention relates to an endoscopic form detection device including an endoscope configured to be inserted into a body cavity and a form detecting method of an inserting section of the endoscope.

2. Description of the Related Art

In recent years, an endoscopic form detection device that can detect a form of an inserting section of an endoscope has been put to practical use. Jpn. Pat. Appln. KOKAI Publication No. 2000-175862 discloses an endoscope insertion form detection device including source coils disposed to an inserting section of an endoscope configured to be inserted into a body cavity. In this endoscope insertion form detection device, positions of the respective source coils are detected by a sense coil provided outside a body. Further, based on the detected positions of the source coils, a form of the inserting section of the endoscope is detected.

Furthermore, Jpn. Pat. Appln. KOKAI Publication No. 2007-319622 discloses an endoscope device including two sensors disposed to an inserting section of an endoscope. In this endoscope device, a sensor on a proximal end side is determined as a reference, and a position and a posture of a sensor on a distal end side are detected. The sensor on the proximal end side is arranged near a proximal end of a bending section, and the sensor on the distal end side is arranged at a distal-end hard section. A bending angle and a bending direction of the bending section are calculated by detecting the position and the posture of the sensor on the distal end side with respect to the sensor on the proximal end side.

Further, Jpn. Pat. Appln. KOKAI Publication No. 11-19027 discloses an endoscopic form detection device including gyroscopes disposed to an inserting section of an endoscope. In this endoscopic form detection device, a posture in a predetermined region (a region to which the gyroscope is disposed) of the inserting section of the endoscope is detected by the gyroscope. Furthermore, a form of the inserting section is detected based on the detected posture in the predetermined region.

BRIEF SUMMARY OF THE INVENTION

According to one aspect of the invention, an endoscopic form detection device includes that an endoscope including an inserting section in which sensor units are arranged in longitudinal directions at intervals of a predetermined inter-sensor dimension; a posture detecting section configured to detect a posture of each of the sensor units based on measurement data in the sensor unit; a linear form detecting section configured to detect a detected linear form of the inserting section of the endoscope on an assumption that a form between the respective sensor units is a linear link whose dimension is equal to the inter-sensor dimension based on the posture of each of the sensor units detected by the posture detecting section; and a curve form detecting section configured to perform curve interpolation with respect to the detected linear form detected by the linear form detecting section on an assumption that a form between the respective sensor units is an arc whose arc length is equal to the inter-sensor dimension, and configured to detect a detected curve form.

According to one another aspect of the invention, a form detecting method of an inserting section of an endoscope, includes that performing measurement by using sensor units arranged in the inserting section of the endoscope in longitudinal directions at intervals of a predetermined inter-sensor dimension; detecting a posture of each sensor unit by using a posture detecting section based on measurement data in the sensor unit; detecting a detected linear form of the inserting section of the endoscope by using a linear form detecting section on the assumption that a form between the respective sensor units is a linear link whose dimension is equal to the inter-sensor dimension based on the posture of each sensor unit detected by the posture detecting section; and performing curve interpolation with respect to the detected linear form detected by the linear form detecting section and forming a detected curve form by using a curve form detecting section on the assumption that a form between the respective sensor units is an arc whose arc length is equal to the inter-sensor dimension.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 7 is a schematic view explaining processing in a link position compensating section of the linear form detecting section according to the first embodiment;

FIG. 8 is a schematic view showing a detected curve form detected by a curve form detecting section of the endoscopic form detection device according to the first embodiment;

FIG. 10 is a schematic view explaining processing in a curve interpolating section of the curve form detecting section according to the first embodiment;

FIG. 11 is a schematic view explaining processing in an arc position compensating section of the curve form detecting section according to the first embodiment;

FIG. 12 is a block diagram showing a configuration of a personal computer of an endoscopic form detection device according to a second embodiment of to the present invention;

FIG. 13 is a flowchart showing a method of detecting a detected curve form by the curve form detecting section of the endoscopic form detection device according to the second embodiment;

FIG. 14 is a schematic view explaining processing in an interpolation sequentially implementing section of the curve form detecting section according to the second embodiment;

FIG. 15 is a schematic view explaining processing in an uninterpolated link position compensating section of the curve form detecting section according to the second embodiment;

FIG. 16 is a block diagram showing a configuration of a personal computer of an endoscopic form detection device according to a first modification of the present invention; and FIG. 17 is a flowchart showing a method of detecting a form of an inserting section of an endoscope in a moving state according to the first modification.

DETAILED DESCRIPTION OF THE INVENTION

First Embodiment

A first embodiment according to the present invention will now be described with reference to FIG. 1 to FIG. 15.

Figure 1:
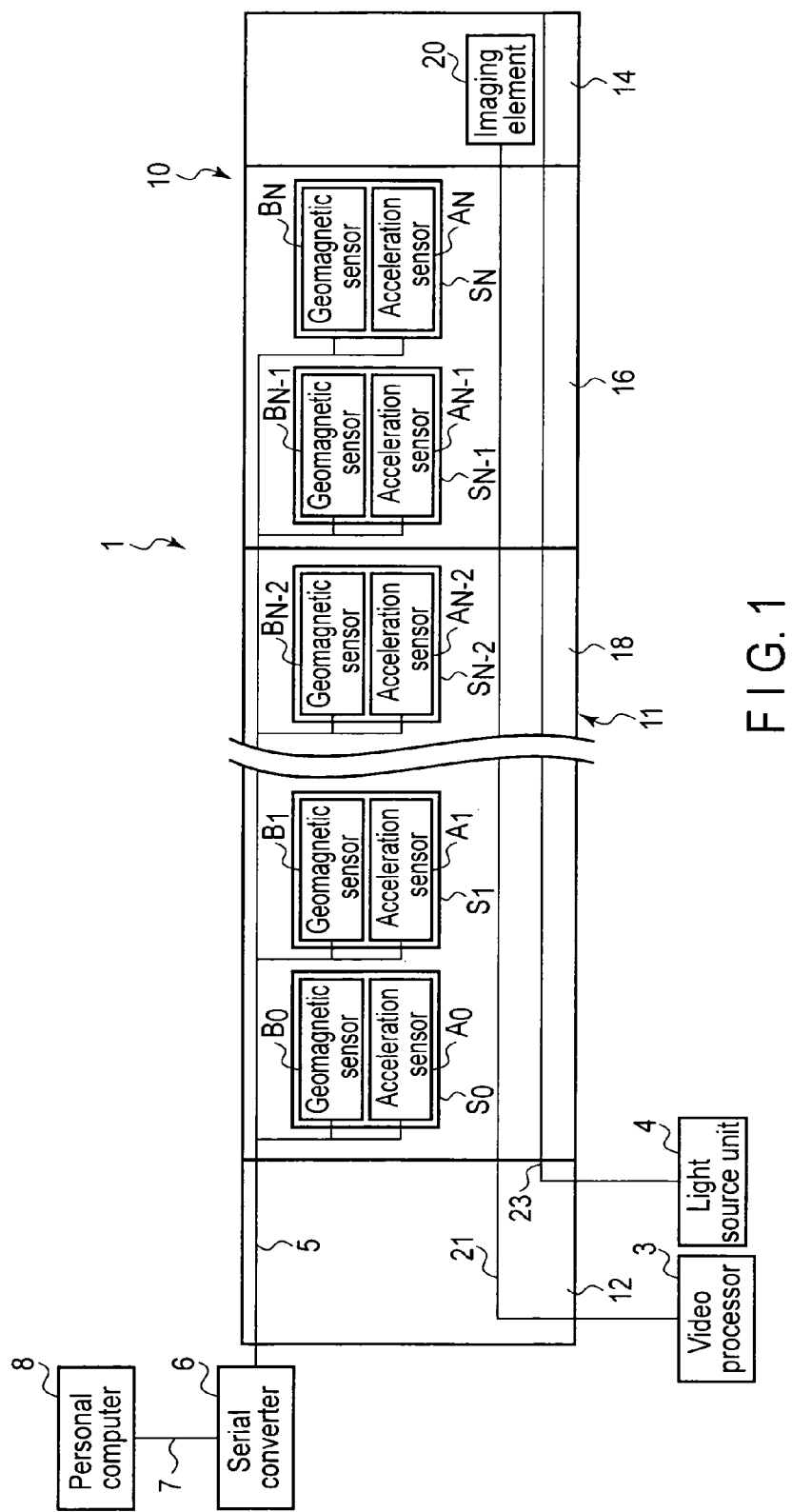
FIG. 1 is a block diagram showing a configuration of an endoscopic form detection device according to a first embodiment of the present invention.

FIG. 1 is a view showing an endoscopic form detection device 1 according to a first embodiment. As shown in FIG. 1, an endoscope 10 of the endoscopic form detection device 1 includes an inserting section 11 configured to be inserted into a body cavity and an operating section 12 provided to a proximal end side of the inserting section 11. The inserting section 11 includes a distal-end hard section 14 provided at a most distal end side; a bending section 16 provided to the proximal end side of the distal-end hard section 14, and an elongated flexible tube section 18 provided to the proximal end side of the bending section 16.

An imaging element 20 such as a CCD configured to image a subject is provided in the distal-end hard section 14. One end of an imaging signal line 21 is connected to the imaging element 20. The imaging signal line 21 is extended to the outside of the endoscope 10 from the operating section 12 through the inserting section 11, and the other end of the imaging signal line 21 is connected to a video processor 3 which is an image processing unit. Furthermore, a light guide 23 configured to guide illumination light applied to a subject is extended to an illumination window (not shown) of the distal-end hard section 14 along longitudinal directions in the inserting section 11. The light guide 23 is extended to the outside of the endoscope 10 from the operating section 12 and connected to a light source unit 4.

Moreover, one end of each of four bending operation wires (not shown) as bending operation transmission members is connected to a distal end portion of the bending section 16 in the inserting section 11. The other end of each bending operation wire is connected to a bending operation knob (not shown), which is a bending operating section provided to the operating section 12, through the flexible tube section 18. The bending operation wires move in the longitudinal directions by operations using the bending operation knob. The bending section 16 is configured to bend in up-down directions and left-right directions of the endoscope 10 by the movement of the bending operation wires.

A plurality of (N+1 in this embodiment) sensor units $S_0$ to $S_N$ are provided in the inserting section 2. The respective sensor units $S_i$ (i=0, 1, 2, ..., N) are arranged to be apart from each other in the longitudinal directions at fixed intervals (=50 mm). That is, respective sensor units $S_i$ are arranged to be apart from each other in the longitudinal directions at intervals of a predetermined inter-sensor dimension l. Here, for example, the sensor unit $S_0$ provided on a most proximal end side is arranged in a proximal end portion of the flexible tube section 18, and the sensor unit $S_N$ provided on the most distal end side is arranged in the distal end portion of the bending section 16. Each sensor unit $S_i$ includes an accelerator sensor $A_i$ configured to measure acceleration, and a geomagnetic sensor $B_i$ configured to measure earth magnetism.

Figure 2:
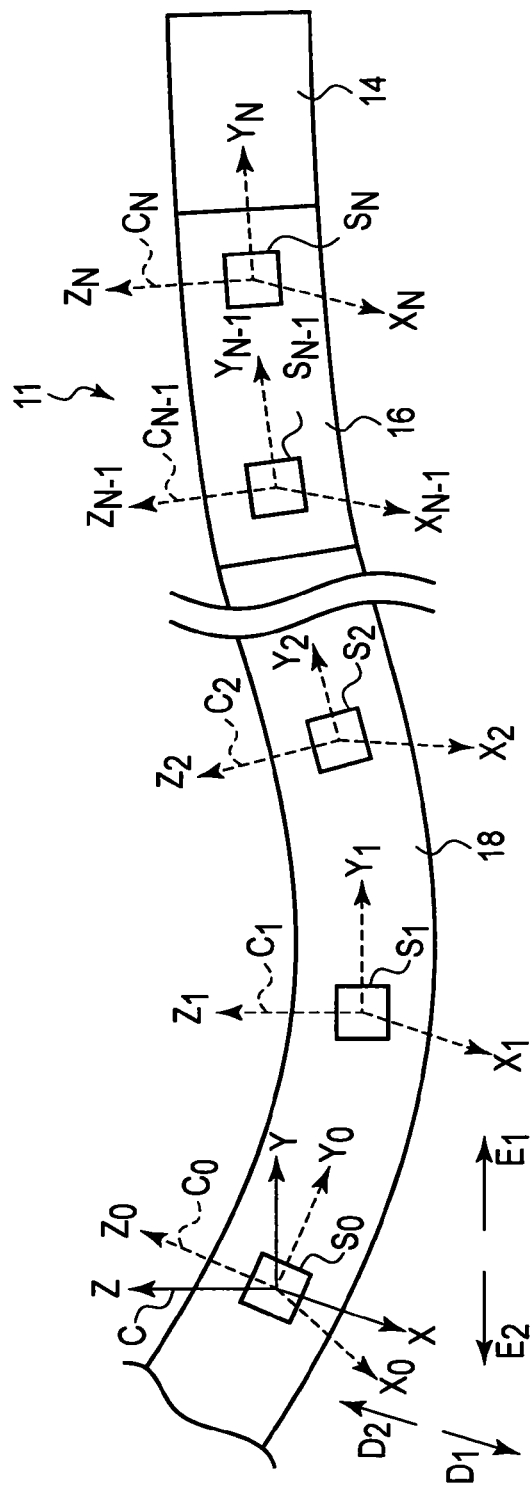
FIG. 2 is a schematic view showing a configuration of an inserting section of an endoscope according to the first embodiment.

FIG. 2 is a view showing the inserting section 11 of the endoscope 10. As shown in FIG. 2, each sensor unit $S_i$ has a local coordinate system $C_i$ (indicated by a dotted line in FIG. 2) having an origin at the center of the sensor unit $S_i$, and also having an $X_i$ axis, a $Y_i$ axis, and a $Z_i$ axis. Here, the $X_i$ axis directions coincide with the left-right directions of the endoscope 10 at the center of the sensor unit $S_i$, and a right direction of the endoscope 10 as seen from the proximal end side is determined to be positive. The $Y_i$ axis directions coincide with the longitudinal directions at the center of the sensor unit $S_i$, and the distal end side direction is determined to be positive. The $Z_i$ axis directions coincide with the up-down directions of the endoscope 10 at the center of the sensor unit $S_i$, and an up direction of the endoscope 10 is determined to be positive. The acceleration sensor $A_i$ is configured to measure an $X_i$ axis directions component, a $Y_i$ axis directions component, and a $Z_i$ axis directions component of acceleration at the origin of the local coordinate system $C_i$.

Furthermore, in the endoscopic form detection device 1, a global coordinate system C (indicated by a solid line in FIG. 2) having an X axis, a Y axis, and a Z axis is defined with the center of the sensor unit $S_0$ provided on the most proximal end side being determined as an origin. Here, the global coordinate system C is a rectangular Cartesian coordinate system for a right-hand system with the center of the sensor unit $S_0$ provided on the most proximal end side determined as an origin. The X-axis directions coincide with predetermined directions (directions parallel to arrows D1 and D2 in FIG. 2 in this embodiment) perpendicular to vertical directions in which gravity functions, and a direction of the arrow D1 in FIG. 2 is determined to be positive. The Y axis directions coincide with directions (directions parallel to arrows E1 and E2 in FIG. 2 in this embodiment) perpendicular to the vertical directions and the X axis directions, and a direction of the arrow E1 in FIG. 2 is determined to be positive. The Z axis directions coincide with the vertical directions, and an up direction (direction extending from a back side to a front side of a paper sheet) of the vertical directions is determined to be positive. It is to be noted that a positive direction of the X axis directions of the global coordinate system is determined as a magnetic north direction for convenience of explanation.

Each local coordinate system $C_i$ is a coordinate system obtained by rotating the global coordinate system C $\alpha_i$ about the X axis, $\beta_i$ about the Y axis, and $\gamma_i$ about the Z axis and parallel translating the origin from the center of the sensor unit $S_0$ provided on the most proximal end side to the center of the sensor unit $S_i$. Here, $\alpha_i$ is referred to as a pitch angle, $\beta_i$ is referred to as a roll angle, $\gamma_i$ is referred to as a yaw angle, and three angles, i.e., the pitch angle $\alpha_i$, the roll angle $\beta_i$, and the yaw angle $\gamma_i$ will be generically referred to as posture angles. A clockwise direction of each posture angle $\alpha_i$, $\beta_i$, or $\gamma_i$ seen from a negative direction of each of the X axis, the Y axis, and the Z axis is determined to be positive. A posture of the sensor unit $S_i$ can be detected by calculating values of the posture angles $\alpha_i$, $\beta_i$, and $\gamma_i$.

As shown in FIG. 1, a serial bus 5 such as I2C is connected to the acceleration sensor $A_i$ and the geomagnetic sensor $B_i$ of each sensor unit $S_i$. The serial bus 5 is extended to the outside of the endoscope 10 from the operating section 12 through the inside of the inserting section 11, and its proximal end is connected to a serial converter 6. The serial converter 6 is configured to convert a serial signal of measurement data input from each sensor unit $S_i$ through the serial bus 5 into a USB signal. One end of a USB cable 7 is connected to the serial converter 6. The other end of the USB cable 7 is connected to a personal computer 8. The USB signal of the measurement data in each sensor unit $S_i$ is configured to be input to the personal computer 8 from the serial converter 6.

Figure 3:
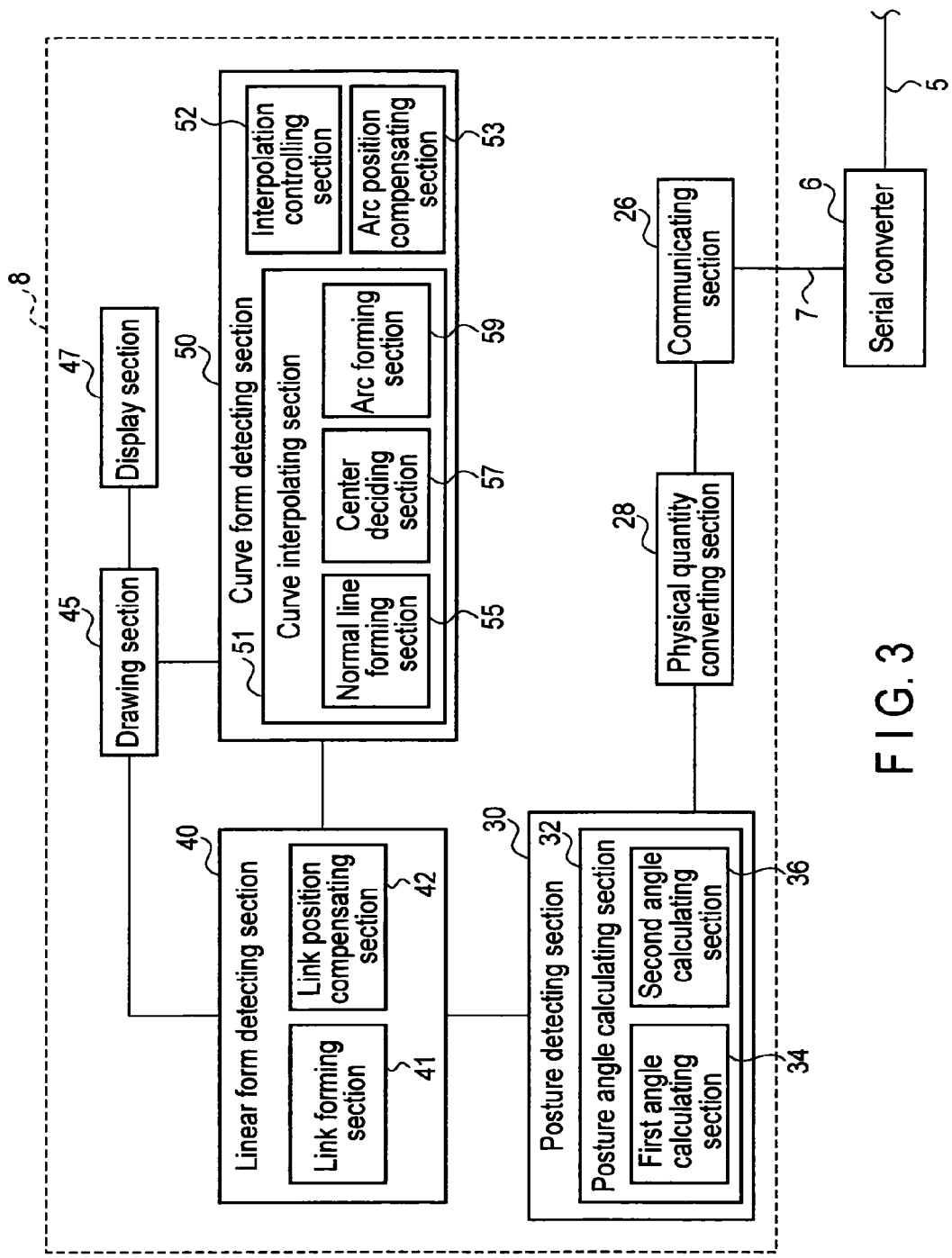
FIG. 3 is a block diagram showing a configuration of a personal computer of the endoscopic form detection device according to the first embodiment.

FIG. 3 is a view showing a configuration of the personal computer 8. As shown in FIG. 3, the personal computer 8 includes a communicating section 26 connected to the serial converter 6 through the USB cable 7. The communicating section 26 is configured to receive the measurement data in each sensor unit $S_i$. A physical quantity converting section 28 is connected to the communicating section 26. The physical quantity converting section 28 is configured to convert the measurement data in each sensor unit $S_i$ received by a communicating section 26 into a physical quantity by using an offset, a gain, and others.

A posture detecting section 30 is connected to the physical quantity converting section 28. The posture detecting section 30 is configured to detect a posture of each sensor unit $S_i$ based on the measurement data in each sensor unit $S_i$. The posture detecting section 30 includes a posture angle calculating section 32 configured to calculate the three posture angles $\alpha_i$, $\beta_i$, and $\gamma_i$ as rotational angles in the local coordinate system $C_i$ of each sensor unit $S_i$ about the X axis, the Y axis, and the Z axis from the global coordinate system C based on measurement data obtained by the acceleration sensor $A_i$ and the geomagnetic sensor $B_i$ of each sensor unit $S_i$. The posture angle calculating section 32 includes a first angle calculating section 34 configured to calculate a pitch angle $\alpha_i$ as a rotational angle in the local coordinate system $C_i$ of each sensor unit $S_i$ about the X axis from the global coordinate system C and a roll angle $\beta_i$ as a rotational angle in the local coordinate system $C_i$ of each sensor unit $S_i$ about the Y axis from the global coordinate system C based on measurement data in the acceleration sensor $A_i$ and the geomagnetic sensor $B_i$ of each sensor unit $S_i$. Moreover, the posture angle calculating section 32 also includes a second angle calculating section 36 configured to calculate a yaw angle $\gamma_i$ as a rotational angle in the local coordinate system $C_i$ of each sensor unit $S_i$ about the Z axis from the global coordinate system C based on the geomagnetic data in the geomagnetic sensor $B_i$ of each sensor unit $S_i$.

Figure 4:
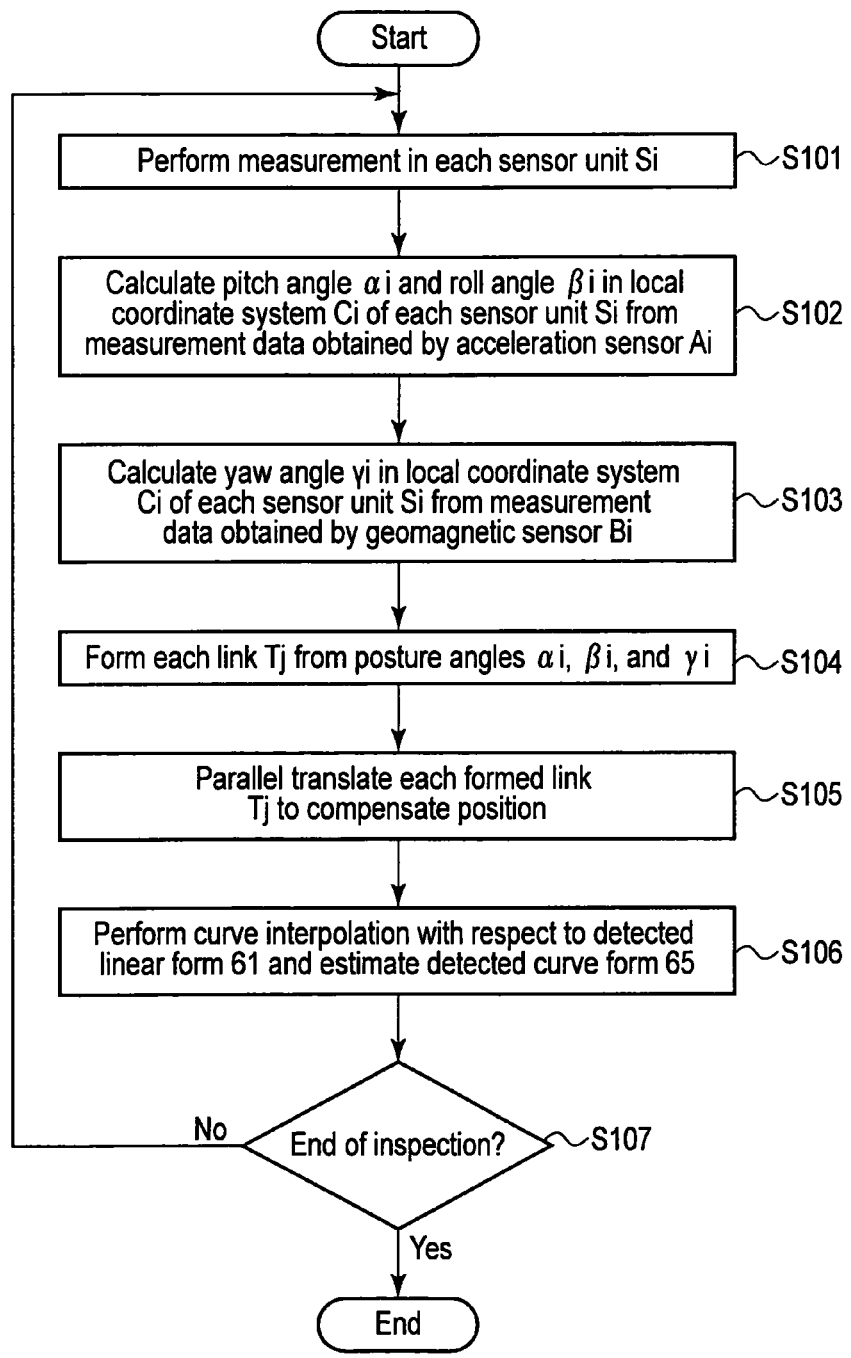
FIG. 4 is a flowchart showing a method of detecting a form of the inserting section of the endoscope in a stationary state according to the first embodiment.

A method of detecting a posture of each sensor unit $S_i$ by the posture detecting section 30 will now be described. FIG. 4 is a flowchart showing a form detecting method of the inserting section 11 in a stationary state in which the inserting section 11 of the endoscope 10 is stopped. As shown in FIG. 4, when detecting a form of the inserting section 11, each sensor unit $S_i$ first performs measurement (a step S101), and the posture detecting section 30 acquires measurement data in each sensor unit $S_i$. Additionally, the posture angle calculating section 32 calculates the three posture angles $\alpha_i$, $\beta_i$, and $\gamma_i$ in the local coordinate system $C_i$ of each sensor unit $S_i$.

When calculating the posture angles $\alpha_i$, $\beta_i$, and $\gamma_i$, the first angle calculating section 34 first calculates the pitch angle $\alpha_i$ and the roll angle $\beta_i$ in the local coordinate system $C_i$ of each sensor unit $S_i$ (a step S102) based on the measurement data in the acceleration sensor $A_i$ of each sensor unit $S_i$. Here, the posture angles $\alpha_i$, $\beta_i$, and $\gamma_i$ are determined as a (Z, X, Y) type that rotates in the order of the yaw angle $\gamma_i$, the pitch angle $\alpha_i$, and the roll angle $\beta_i$. Therefore, a rotation matrix from the global coordinate system C to the local coordinate system $C_i$ is as follows:

$$C_{Bi}^G = R_{Zi} R_{Xi} R_{Yi} = \begin{bmatrix} \cos\gamma_i & -\sin\gamma_i & 0 \\ \sin\gamma_i & \cos\gamma_i & 0 \\ 0 & 0 & 1 \end{bmatrix} \begin{bmatrix} 1 & 0 & 0 \\ 0 & \cos\alpha_i & -\sin\alpha_i \\ 0 & \sin\alpha_i & \cos\alpha_i \end{bmatrix} \begin{bmatrix} \cos\beta_i & 0 & \sin\beta_i \\ 0 & 1 & 0 \\ -\sin\beta_i & 0 & \cos\beta_i \end{bmatrix} \quad (1)$$

$$= \begin{bmatrix} -\sin\gamma_i \cdot \sin\alpha_i \cdot \sin\beta_i + \cos\beta_i \cdot \cos\gamma_i & -\sin\gamma_i \cdot \cos\alpha_i & \sin\gamma_i \cdot \sin\alpha_i \cdot \cos\beta_i + \sin\beta_i \cdot \cos\gamma_i \\ \cos\gamma_i \cdot \sin\alpha_i \cdot \sin\beta_i + \cos\beta_i \cdot \sin\gamma_i & \cos\gamma_i \cdot \cos\alpha_i & -\cos\gamma_i \cdot \sin\alpha_i \cdot \cos\beta_i + \sin\beta_i \cdot \sin\gamma_i \\ -\cos\alpha_i \cdot \sin\beta_i & \sin\alpha_i & \cos\alpha_i \cdot \cos\beta_i \end{bmatrix}$$

In the stationary state in which the inserting section 11 is stopped, gravitational acceleration alone functions downward in the vertical directions. That is, in both the global coordinate system C and the local coordinate system $C_i$, the gravitational acceleration alone functions downward in the vertical directions. Therefore, at this time, an X axis directions component, a Y axis directions component, and a Z axis directions component of an acceleration vector in the global coordinate system C are as follows:

$$\dot{a}_{th} = [0\ 0\ -g]^T \quad (2)$$

Further, it is assumed that an $X_i$ axis directions component, a $Y_i$ axis directions component, and a $Z_i$ axis directions component of an acceleration vector in the local coordinate system $C_i$ measured by the acceleration sensor Ai are as follows:

$$\dot{a}_{obsi} = [a_{Bi\_X}\ a_{Bi\_Y}\ a_{Bi\_Z}]^T \quad (3)$$

Here, the local coordinate system $C_i$ is a coordinate system obtained by rotating the global coordinate system C in the order of the yaw angle $\gamma_i$, the pitch angle $\alpha_i$, and the roll angle $\beta_i$. Therefore, based on Expression (1) to Expression (3), acceleration components observed in the local coordinate system $C_i$ are as follows:

$$\dot{a}_{obsi} = (C_{Bi}^G)^T \dot{a}_{th} = -g \begin{bmatrix} -\cos\alpha_i \cdot \sin\beta_i \\ \sin\alpha_i \\ \cos\alpha_i \cdot \cos\beta_i \end{bmatrix} \quad \begin{matrix}(4.1)\\(4.2)\\(4.3)\end{matrix}$$

Here, when a square of Expression (4.1) is added to a square of Expression (4.2), the following expression can be obtained:

$$a_{Bi\_X}^2 + a_{Bi\_Z}^2 = g^2 \cos^2\alpha_i (\sin^2\beta_i + \cos^2\beta_i) \quad (5)$$

Further, the following expression is derived:

$$g\cos\alpha_i = \sqrt{a_{Bi\_X}^2 + a_{Bi\_Z}^2} \quad (6)$$

Furthermore, when Expression (4.2) is divided by Expression (6), the following expression can be obtained:

$$\alpha_i = \tan^{-1}\left(\frac{-a_{Bi\_Y}}{\sqrt{a_{Bi\_X}^2 + a_{Bi\_Z}^2}}\right) \quad (7)$$

As a result, the pitch angle $\alpha_i$ in the local coordinate system $C_i$ can be obtained. Moreover, when Expression (4.1) is divided by Expression (4.3), the following expression can be obtained:

$$\beta_i = \tan^{-1}\left(\frac{-a_{Bi\_X}}{a_{Bi\_Z}}\right) \quad (8)$$

The roll angle $\beta_i$ in the local coordinate system $C_i$ can be derived. As described above, based on measurement data in each acceleration sensor $A_i$, the pitch angle $\alpha_i$ and the roll angle $\beta_i$ in the local coordinate system $C_i$ can be calculated.

Figure 5:
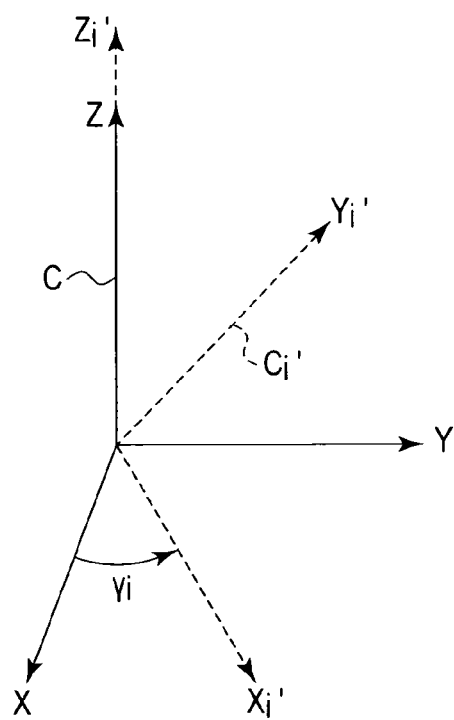
FIG. 5 is a schematic view showing a global coordinate system and a corrected coordinate system of the endoscopic form detection device according to the first embodiment in comparison to each other.

Additionally, the second angle calculating section 36 calculates the yaw angle $\gamma_i$ in the local coordinate system $C_i$ of each sensor unit Si based on measurement data obtained by the geomagnetic sensor $B_i$ of each sensor unit $S_i$ (a step S103). Here, a corrected coordinate system $C'_i$ obtained by correcting the rotation from the global coordinate system C about the X axis and the rotation from the global coordinate system C about the Y axis in each local coordinate system $C_i$ is defined by using the pitch angle $\alpha_i$ and the roll angle $\beta_i$ calculated at the step S102. FIG. 5 is a view showing the global coordinate system C (indicated by a solid line in FIG. 5) and the corrected coordinate system $C'_i$ (indicated by a dotted line in FIG. 5). It is to be noted that the global coordinate system C and the corrected coordinate system $C'_i$ actually have origins provided at different positions, and FIG. 5 shows a state in which the origins are provided at the same position in order to compare both the coordinate systems. As shown in FIG. 5, the corrected coordinate system $C'_i$ obtained by correcting the rotation about the X axis and the rotation about the Y axis is a coordinate system obtained by rotating the global coordinate system C by the yaw angle $\gamma_i$ about the Z axis and has an $X'_i$ axis, a $Y'_i$ axis, and a $Z'_i$ axis. $X'_i$ directions and $Y'_i$ axis directions coincide with directions rotated by the yaw angle γi about the Z axis from the X axis directions and the Y axis directions in the global coordinate system C, respectively. $Z'_i$ axis directions coincide with the vertical directions, i.e., the Z axis directions in the global coordinate system C. Here, since the positive direction of the X axis directions in the global coordinate system C coincides with the magnetic north direction, a positive direction of the $X'_i$ directions is a direction rotated by the yaw angle $\gamma_i$ about the Z axis from the magnetic north direction.

It is assumed that an $X_i$ axis directions component, a $Y_i$ axis directions component, and a $Z_i$ axis directions component of a geomagnetic vector in the local coordinate system $C_i$ measured by the geomagnetic sensor $B_i$ are as follows:

$$\dot{m}_{obsi} = [M_{Xi} M_{Yi} M_{Zi}]^T \quad (9)$$

The corrected coordinate system $C'_i$ is a coordinate system obtained by correcting the rotation from the global coordinate system C about the X axis and the rotation from the global coordinate system C about the Y axis in the local coordinate system $C_i$. Therefore, based on $R_{xi}$ and $R_{yi}$ in Expression (1) and Expression (9), an $X'_i$ axis directions component, a $Y'_i$ axis directions component, and a $Z'_i$ axis directions component in the corrected coordinate system $C'_i$ of a geomagnetic vector measured by the geomagnetic sensor $B_i$ are as follows:

$$\begin{aligned}\dot{m}'_{obsi} &= R_{Xi}R_{Yi}\dot{m}_{obsi} \\ &= \begin{bmatrix} 1 & 0 & 0 \\ 0 & \cos\alpha_i & -\sin\alpha_i \\ 0 & \sin\alpha_i & \cos\alpha_i \end{bmatrix}\begin{bmatrix} \cos\beta_i & 0 & \sin\beta_i \\ 0 & 1 & 0 \\ -\sin\beta_i & 0 & \cos\beta_i \end{bmatrix}\begin{bmatrix} M_{Xi} \\ M_{Yi} \\ M_{Zi} \end{bmatrix} \\ &= \begin{bmatrix} \cos\beta_i & 0 & \sin\beta_i \\ \sin\alpha_i\sin\beta_i & \cos\alpha_i & -\sin\alpha_i\cos\beta_i \\ -\cos\alpha_i\sin\beta_i & \sin\alpha_i & \cos\alpha_i\cos\beta_i \end{bmatrix}\begin{bmatrix} M_{Xi} \\ M_{Yi} \\ M_{Zi} \end{bmatrix}\end{aligned} \quad (10.1)$$

$$\dot{m}'_{obsi} = [M'_{Xi} \ M'_{Yi} \ M'_{Zi}]^T \quad (10.2)$$

Based on Expression (10.1) and Expression (10.2), the following expressions can be obtained:

$$M_{Xi}' = M_{Xi}\cos\beta_i + M_{Zi}\sin\beta_i \quad (11.1)$$

$$M_{Yi}' = M_{Yi}\cos\alpha_i + \sin\alpha_i(M_{Xi}\sin\beta_i - M_{Zi}\cos\beta_i) \quad (11.2)$$

A geomagnetic component on a horizontal plane (an $X'_i$-$Y'_i$ plane in the corrected coordinate system $C'_i$) perpendicular to the vertical directions directs the magnetic north direction. Therefore, based on Expression (11.2) and Expression (11.2), an angle $\theta_i$ from the $X'_i$ axis to the magnetic north direction can be obtained by using the $X'_i$ axis component and the $Y'_i$ axis component of the geomagnetic vector in the corrected coordinate system $C'_i$. That is, the following expression can be obtained:

$$\theta_i = \tan^{-1}(M_{Yi}'/M_{Xi}') \quad (12)$$

In regard to the angle $\theta_i$, a clockwise direction when seeing the $Z'_i$ axis (the Z axis) from a negative direction is determined to be positive. Here, the corrected coordinate system $C'_i$ is a coordinate system obtained by rotating the global coordinate system C the yaw angle $\gamma_i$ about the Z axis. Therefore, the angle $\theta_i$ obtained based on Expression (12) is the yaw angle $\gamma_i$ in the local coordinate system $C_i$ when the global coordinate system C is determined as a reference.

It is to be noted that, when one of the X axis directions in the global coordinate system C does not coincide with the magnetic north direction, the yaw angle $\gamma_i$ can be likewise obtained with reference to the magnetic north. An X axis directions component, a Y axis directions component, and a Z axis directions component of the geomagnetic vector in the global coordinate system C are determined as follows:

$$\dot{m}_{th} = [E_X E_Y E_Z]^T \quad (13)$$

The X axis directions component, the Y axis directions component, and the Z axis directions component of the geomagnetic vector in the global coordinate system C can be obtained by using a geomagnetic sensor which is of the same type as the geomagnetic sensor $B_i$ to conduct the measurement in a state in which the X axis directions, the Y axis directions, and the Z axis directions in the global coordinate system C coincide with axis directions. Further, based on Expression (13), an angle θ from the X axis to the magnetic north direction is obtained by using the X axis component and the Y axis component of the geomagnetic vector in the global coordinate system C. That is, the following expression can be acquired:

$$\theta = \tan^{-1}(E_Y/E_X) \quad (14)$$

Here, in regard to the angle θ, the clockwise direction when the Z axis is seen from the negative direction is determined to be positive. The corrected coordinate system $C'_i$ is a coordinate system obtained by rotating the global coordinate system C by the yaw angle $\gamma_i$ about the Z axis. Therefore, based on Expression (12) and Expression (14), the following representation can be achieved:

$$\gamma_i = \theta - \theta_i \quad (15)$$

As a result, when the global coordinate system C is determined as a reference the yaw angle $\gamma_i$ of the local coordinate system $C_i$ can be obtained.

As described above, based on the measurement data in each geomagnetic sensor $B_i$, the yaw angle $\gamma_i$ of each local coordinate system $C_i$ is calculated. Based on the calculated values of the posture angles $\alpha_i$, $\beta_i$, and $\gamma_i$, the posture detecting section 30 is configured to detect a posture of each sensor unit $S_i$.

Figure 6:
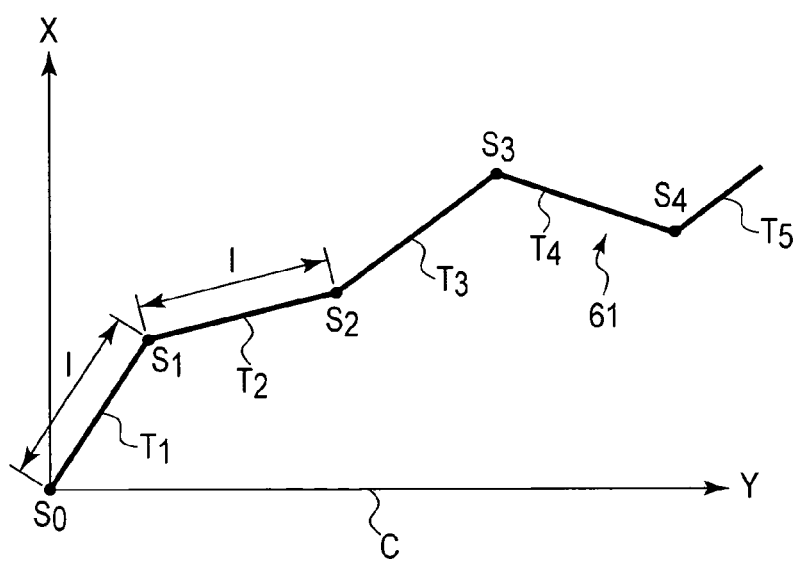
FIG. 6 is a schematic view showing a detected linear form detected by a linear form detecting section of the endoscopic form detection device according to the first embodiment.

As shown in FIG. 3, a linear form detecting section 40 is connected to the posture detecting section 30. FIG. 6 is a view showing a detected linear form 71 of the inserting section 11 of the endoscope 10 detected by the linear form detecting section 40 from the negative direction of the Z axis in the global coordinate C. As shown in FIG. 6, the linear form detecting section 40 is configured to detect the detected linear form 71 of the inserting section 11 on the assumption that a form between the respective sensor units $S_i$ is a linear link $T_j$ (j=, 1, 2, ... N) whose dimension is equal to the inter-sensor dimension 1 based on the posture of each sensor unit $S_i$ detected by the posture detecting section 30. Here, the kth link $T_k$ from the proximal end side is a link between the kth sensor unit $S_{k-1}$ from the proximal end side and the (K+1)th sensor unit $S_k$ from the proximal end side. The linear form detecting section 40 includes a link forming section 41 configured to form each link $T_j$, and a link position compensating section 42 configured to parallel translate each link $T_j$ formed by the link forming section 41 to compensate a position of the link $T_j$. The link position compensating section 42 is configured to parallel translate each link $T_j$ in such a manner that link boundaries between the link $T_j$ and adjacent links $T_{j-1}$ and $T_{j+1}$ become continuous.

A drawing section 45 is connected to the linear form detecting section 40. A display section 47 is connected to the drawing section 45. The detected linear form 71 of the inserting section 11 in the global coordinate system C detected by the linear form detecting section 40 is configured to be drawn by the drawing section 45. An operator can confirm the detected linear form 71 drawn by the drawing section 45 in the display section 47.

A method of detecting the detected linear form 71 of the inserting section 11 in the linear form detecting section 40 will now be described. As shown in FIG. 4, when detecting the detected linear form 71 of the inserting section 11, the link forming section 41 first forms each link $T_j$ having the linear form based on the values of the posture angles $\alpha_i$, $\beta_i$, and $\gamma_i$ calculated at the steps S102 and S103 (a step S104). Here, description will be given as to formation of a kth link $T_k$ from the proximal end side between a kth sensor unit $S_{k-1}$ from the proximal end side and a (k+1)th sensor unit $S_k$ from the proximal end side.

As represented by Expression (7), Expression (8), and Expression (12) (or Expression (15)), posture angles $\alpha_{k-1}$, $\beta_{k-1}$, and $\gamma_{k-1}$ in a local coordinate system $C_{k-1}$ (i.e., the link) are calculated at the steps S102 and S103. Each of the posture angles $\alpha_{k-1}$, $\beta_{k-1}$, and $\gamma_{k-1}$ and the inter-sensor dimension l which is between each of the sensor units $S_i$ can be used to obtain a coordinate $P'_k(l_{xk}, l_{yk}, l_{zk})$ of the sensor unit $S_k$ when the sensor unit $S_{k-1}$ is placed at the origin of the global coordinate system C. Here, the coordinate $P'_k$ is represented as follows:

$$l_k = [\,l_{xk}\ l_{yk}\ l_{zk}\,]^T = lC^G_{Bk-1}e_{yk-1} = l\begin{bmatrix} -\sin\gamma_{k-1} \cdot \cos\alpha_{k-1} \\ \cos\gamma_{k-1} \cdot \cos\alpha_{k-1} \\ \sin\alpha_{k-1} \end{bmatrix} \quad (16.1)$$

$$e_{yk-1} = [\,0\ 1\ 0\,]^T \quad (16.2)$$

In Expression (16.1) and Expression (16.2), $e_{yk-1}$ is a unit vector in $Y_{k-1}$ axis directions which are the longitudinal directions at the origin of the local coordinate system $C_{k-1}$. When the unit vector $e_{yk-1}$ is multiplied by a rotation matrix calculated by Expression (1), an X axis directions component, a Y axis directions component, and a Z axis directions component of the unit vector $e_{yk-1}$ in the global coordinate system C can be calculated, respectively. That is, $l_{xk}$, $l_{yk}$, and $l_{zk}$ are components obtained by dividing a vector having a magnitude l in the $Y_{k-1}$ axis directions in the local coordinate system $C_{k-1}$ to the X axis directions, the Y axis directions, and the Z axis directions in the global coordinate system C, respectively. The link $T_k$ is formed by linearly connecting the origin of the global coordinate system C with the coordinate $P'_k(l_{xk}, l_{yk}, l_{zk})$ calculated by Expression (16.1) and Expression (16.2).

It is to be noted that each link $T_j$ other than the link $T_k$ is likewise formed by the link forming section 41. That is, Expression (16.1) and Expression (16.2) are used to obtain a coordinate $P'_j(l_{xj}, l_{yj}, l_{zj})$ of the sensor unit $S_j$ on the distal end side (the side far from the origin of the global coordinate system C) of the link $T_j$ when the sensor unit $S_{j-1}$ on the proximal end side (the side close to the origin of the global coordinate system C) of the link $T_j$ is placed at the origin of the global coordinate system C. Further, the link $T_j$ is formed by linearly connecting the origin of the global coordinate system C to the coordinate $P'_j(l_{xj}, l_{yj}, l_{zj})$. That is, the link forming section 41 is configured to form the link $T_j$ on the assumption that the link $T_j$ is extended in the longitudinal directions at the center of the sensor unit $S_{j-1}$ on the proximal end side from the center of the sensor unit $S_{j-1}$ on the proximal end side (the side close to the origin of the global coordinate system C) to the center of the sensor unit $S_j$ on the distal end side (the side far from the origin of the global coordinate system C).

Furthermore, it is preferable for the inter-sensor dimension l to be approximately 50 mm. When the inter-sensor dimension l is increased, the number of the sensor units $S_i$ is reduced, thereby decreasing a cost. Moreover, when the inter-sensor dimension l is smaller than approximately 50 mm, an error when detecting a form of the inserting section 11 can be reduced even if the interval between the respective sensor units $S_i$ is assumed to be the linear link $T_j$ whose dimension is equal to the inter-sensor dimension l.

Additionally, the link position compensating section 42 is configured to correct a position of the link $T_j$ by parallel translating each link $T_j$ formed by the link forming section 41 in such a manner that link boundaries between the link $T_j$ and adjacent links $T_{j-1}$ and $T_{j+1}$ become continuous (a step S105). FIG. 7 is a view explaining processing in the link position compensating section 42. Here, description will be given as to positional compensation of the kth link $T_k$ from the proximal end side between the kth sensor unit $S_{k-1}$ from the proximal end side and the (k+1)th sensor unit $S_k$ from the proximal end side.

As shown in FIG. 7, in a state before the link position compensating section 42 performs positional compensation of the link $T_k$, the positional compensation is completed from the first link to the link $T_{k-1}$ adjacent to the proximal end side of the link $T_k$, and a link positional compensation completed portion 73 is formed. When performing the positional compensation of the link $T_k$, the link position compensating section 42 parallel translates the link $T_k$ a distance from the origin to the distal end of the link positional compensation completed portion 73. That is, the link $T_k$ is parallel translated from a position indicated by a dotted line in FIG. 7 to a position indicated by a solid line in FIG. 7. As a result, a link boundary between the link $T_{k-1}$ and the link $T_k$ becomes continuous, and the position of the link $T_k$ is thereby compensated.

It is to be noted that a position of each link $T_j$ other than the link $T_k$ is likewise compensated. That is, when performing the positional compensation of the link $T_j$, the link position compensating section 42 is configured to parallel translate the link $T_j$ a distance from the origin to the distal end (the end on the side far from the origin of the global coordinate system C) of the link positional compensation completed portion 73. As a result, a link boundary between the link $T_j$ and a link $T_{j-1}$ adjacent to the proximal end side (the side close to the origin of the global coordinate system C) of the link $T_j$ becomes continuous, and a position of the link $T_j$ is thereby compensated. However, a position of a link $T_1$ is not compensated since a proximal end of the link $T_1$ is the origin of the global coordinate system C.

As shown in FIG. 3, a linear form detecting section 40 is connected to a curve form detecting section 50. FIG. 8 is a view showing a detected curve form 65 of the inserting section 11 of the endoscope 10 detected by the curve form detecting section 50 from a positive direction of the Z axis of the global coordinate system C. As shown in FIG. 8, the curve form detecting section 50 is configured to perform curve interpolation with respect to the detected linear form 61 on the assumption that a form between respective sensor units $S_i$ is an arc $L_j$ (j=1, 2, . . . N) whose arc length is equal to the inter-sensor dimension l. The detected curve form 65 is formed by performing the curve interpolation. Here, a kth arc $L_k$ from the proximal end side is an arc between a kth sensor unit $S_{k-1}$ from the proximal end side and a (k+1)th sensor unit $S_k$ from the proximal end side.

The curve form detecting section 50 includes a curve interpolating section 51 configured to perform the curve interpolation in accordance with each link $T_j$ to form the arc $L_j$, an interpolation controlling section 52 configured to control the curve interpolating section 51 to perform the curve interpolation with respect to all the links $T_j$, and an arc position compensating section 53 configured to parallel translate each arc $L_j$ formed by the curve interpolating section 51 to compensate a position of the arc $L_j$. The arc position compensating section 53 is configured to translate each arc $L_j$ in such a manner that arc boundaries between the arc $L_j$ and adjacent arcs $L_{j-1}$ and $L_{j+1}$ become continuous.

As shown in FIG. 3, the curve interpolating section 51 includes a normal line forming section 55, a center deciding section 57, and an arc forming section 59. Details of the normal line forming section 55, the center deciding section 57, and the arc forming section 59 will be described later.

The drawing section 45 is connected to the curve form detecting section 50. The detected curve form 65 of the inserting section 11 in the global coordinate system C formed by the curve form detecting section 50 is drawn by the drawing section 45. An operator can confirm the detected curve form 65 drawn by the drawing section 45 in the display section 47.

Here, description will be given as to a method of performing the curve interpolation with respect to the detected linear form 61 detected by the linear form detecting section 40 to detect the detected curve form 65. As shown in FIG. 4, the curve form detecting section 50 is configured to carry out the curve interpolation of the detected linear form 61 on the assumption that a form between the respective sensor units $S_i$ is the arc $L_j$ whose arc length is equal to the inter-sensor dimension l, and configured to estimate the detected curve form 65 (a step S106). As described above, if the inter-sensor dimension l is smaller than approximately 50 mm, the error in the detection of the form of the inserting section 11 is small even though the portion between the respective sensor units $S_i$ is the linear link $T_j$ whose dimension is equal to the inter-sensor dimension l. However, a form of the inserting section 11 of the endoscope 10 when inserted into a body cavity is a curve form. Therefore, it is important to perform the curve interpolation of the detected linear form 61. Here, although there are differences among products, the inserting section 11 of the endoscope 10 has appropriate elasticity. Therefore, a curvature of the curved form of the inserting section 11 varies only slightly. Therefore, when the curve interpolation is performed on the assumption that the form between the sensor units $S_i$ is the arc $L_j$ having a radius $R_j$ (curvature/$R_j$), it is possible to form the detected curve form 65 having a small error from an actual curve form of the inserting section 11.

When performing the curve interpolation of the detected linear form 61 to detect the detected curve form 65, the curve interpolating section 51 is configured to carry out the curve interpolation in accordance with each link $T_j$ to form the arc $L_j$. Here, a method of performing the curve interpolation of the link $T_j$ by the curve interpolating section 51 will be explained. Here, description will be given as to the curve interpolation of a kth link $T_k$ from the proximal end side between a kth sensor unit $S_{k-1}$ from the proximal end side and a (k+1)th sensor unit $S_k$ from the proximal end side.

Figure 9:
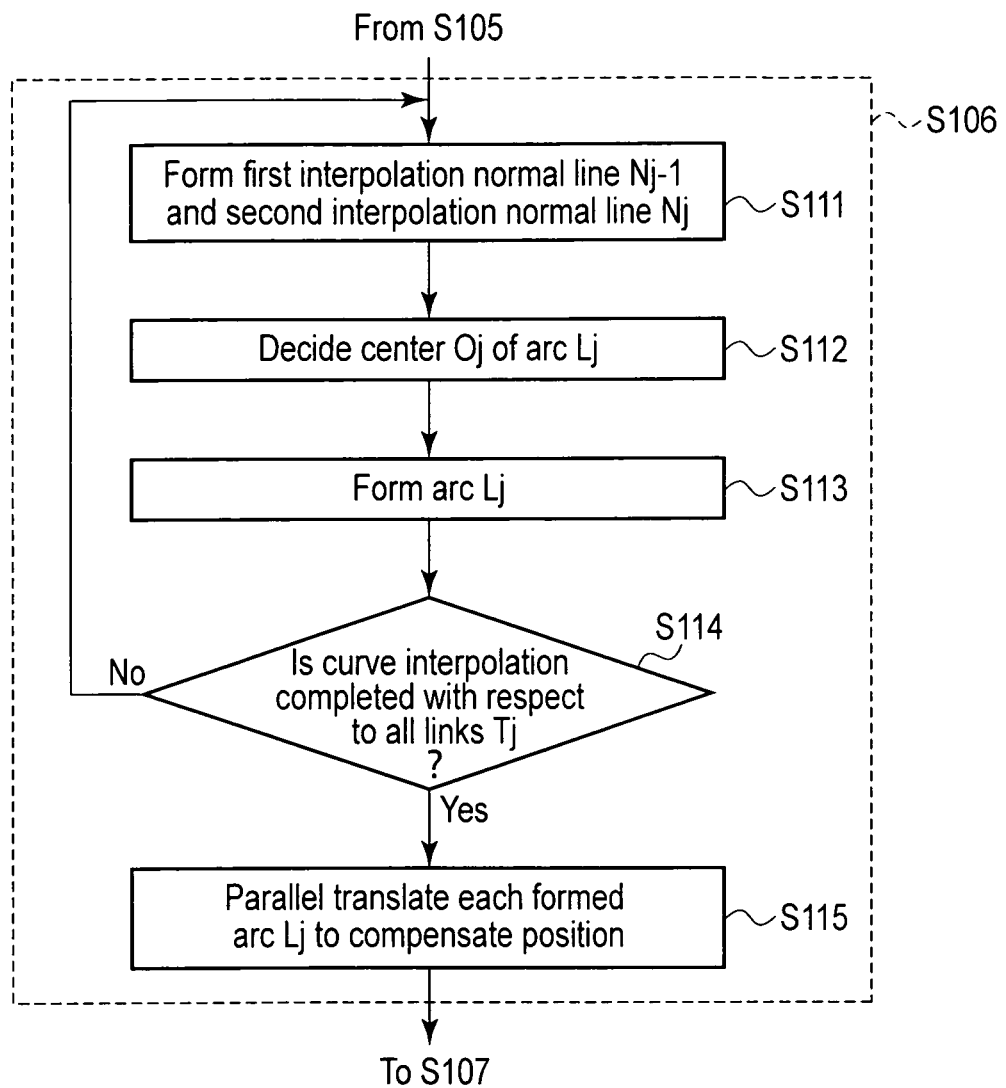
FIG. 9 is a flowchart showing a method of detecting the detected curve form by the curve form detecting section according to the first embodiment.

FIG. 9 is a flowchart showing a method of using the curve form detecting section 50 to detect the detected curve form 65 from the detected linear form 61. FIG. 10 is a view explaining processing in the curve interpolating section 51. As shown in FIG. 10, in a state before the curve interpolation of the link (an interpolation target link) $T_k$ as an interpolation target is carried out by the curve interpolating section 51, the sensor unit $S_k$ is placed at a point $Q'_k$. As shown in FIG. 9 and FIG. 10, when performing the curve interpolation of the link (the interpolation target link) $T_k$ by the curve interpolating section 51, the normal line forming section 55 is configured to first form a first interpolation normal line $N_{k-1}$ that runs through a proximal end (a first end point) of the link $T_k$ and is perpendicular to the link $T_k$ and a second interpolation normal line $N_k$ that runs through a distal end (a second end point) of the link $T_k$ and is perpendicular to a link (an interpolation target adjacent link) $T_{k+1}$ adjacent to the distal end side of the link $T_k$ (a step S111). That is, the first interpolation normal line $N_{k-1}$ can be obtained under conditions that it is perpendicular to a directional vector of the link $T_k$ and that it runs through the sensor unit (the first endpoint) $S_{k-1}$. Likewise, the second interpolation normal line $N_k$ can be obtained under conditions that it is perpendicular to a directional vector of the link $T_{k+1}$ and that it runs through the sensor unit (a second end point) $S_k$.

Furthermore, the center deciding section 57 is configured to calculate an intersection $O_k$ of the first interpolation normal line $N_{k-1}$ and the second interpolation normal line $N_k$ and to decide the intersection $O_k$ as the center of an arc $L_k$ (a step S112). If the first interpolation normal line $N_{k-1}$ and the second interpolation normal line $N_k$ do not cross each other, an intermediate point $O_k$ of two points that minimize a distance between the first interpolation normal line $N_{k-1}$ and the second interpolation normal line $N_k$ is calculated. When calculating the intermediate point $O_k$, an equation of a straight line (not shown) perpendicular to both the first interpolation normal line $N_{k-1}$ and the second interpolation normal line $N_k$ is first obtained. Further, an intersection of this straight line and the first interpolation normal line $N_{k-1}$ and an intersection of this straight line and the second interpolation normal line $N_k$ are obtained, and an intermediate point of the two intersections is the intermediate point $O_k$. Moreover, the intermediate point $O_k$ is determined as the center $O_k$ of the arc $L_k$ (a step S112).

Additionally, the arc forming section 59 is configured to form the arc $L_k$ (a step S113). The arc $L_k$ has a radius $R_k$ equal to a distance between the center $O_k$ decided by the center deciding section 57 and the proximal end (the first end point) of the link (the interpolation target link) $T_k$. That is, the arc $L_k$ has curvature $1/R_k$. Further, the ark $L_k$ is the arc $L_k$ whose arc length starting from the proximal end (the first end point) of the link $T_k$ is equal to the inter-sensor dimension l. A distal end $Q_k$ of the arc $L_k$ is a position of the sensor unit $S_k$ after the curve interpolation. That is, the position of the sensor unit $S_k$ moves from the point $Q'_k$ to the point $Q_k$ by the curve interpolation of the link $T_k$. As described above, the curve interpolation of the link $T_k$ is performed.

It is to be noted that the curve interpolation is likewise carried out with respect to each link $T_j$ other than the link $T_k$ by the curve interpolating section 51. That is, when performing the curve interpolation of the link (an interpolation target link) $T_j$, the normal line forming section 55 is configured to form a first interpolation normal line $N_{j-1}$ that runs through a first end point which is a proximal end (an end on a side close to the origin of the global coordinate C) of the link $T_j$ and is perpendicular to the link $T_j$ and a second interpolation normal line $N_j$ that runs through a second end point which is a distal end (an end on a side far from the origin of the global coordinate C) of the link $T_j$ and is perpendicular to a link (an interpolation target adjacent link) $T_{j+1}$ adjacent to the distal end side (the side far from the origin of the global coordinate C) of the link $T_j$ (the step S111). Furthermore, the center deciding section 57 is configured to calculate an intersection $O_j$ of the first interpolation normal line $N_{j-1}$ and the second interpolation normal line $N_j$ or an intermediate point $O_j$ of two points that minimize a distance between the first interpolation normal line $N_{j-1}$ and the second interpolation normal line $N_j$, and configured to decide the intersection $O_j$ or the intermediate point $O_j$ as the center $O_j$ of an arc $L_j$ (the step S112). Moreover, the arc forming section 59 is configured to form the arc $L_j$ whose radium $R_j$ is equal to a distance between the center $O_j$ and the proximal end of the link (the interpolation target link) $T_j$ and whose arc length starting from the proximal end of the link $T_j$ is equal to the inter-sensor dimension l (the step S113).

Additionally, as shown in FIG. 9, the interpolation controlling section 52 is configured to confirm whether the curve interpolation has been completed with regard to all the links $T_j$ (a step S114). When the curve interpolation has been completed with respect to all the links $T_j$, the processing advances to the next step (the step S114—Yes). When the curve interpolation has not been completed in regard to all the links $T_j$, the processing returns to the step S111 (the step S114—No), and the curve interpolating section 51 is configured to perform the curve interpolation with respect to the links $T_j$ which have not been subjected to the curve interpolation. That is, the curve interpolating section 51 is configured to be controlled to carry out the steps S111 to S113 until the curve interpolation is completed with respect to all the links $T_j$ (N links in this embodiment).

When the curve interpolation has been effected with respect to all the links $T_j$ by the curve interpolating section 51, each arc $L_j$ formed by the curve interpolating section 51 is parallel translated by the arc position compensating section 53 in such a manner that arc boundaries between the arc $L_j$ and adjacent arcs $L_{j-1}$ and $L_{j+1}$ become continuous, thereby compensating a position of the arc $L_j$ (a step S115). FIG. 11 is a view explaining processing in the arc position compensating section 53. Here, description will be given as to positional compensation of the kth arc $L_k$ from the proximal end side between the kth sensor unit $S_{k-1}$ from the proximal end side and the sensor unit $S_k$ from the proximal end side.

As shown in FIG. 11, in a state before the positional compensation of the arc $L_k$ is carried out by the arc position compensating section 53, the positional compensation from the first arc to an arc $L_{k-1}$ adjacent to the proximal end side of the arc $L_k$ has been completed, whereby an arc positional compensation completed portion 67 is formed. When carrying out the positional compensation of the arc $L_k$, the arc position compensating section 53 is configured to parallel translate the arc $L_k$ a distance from the proximal end of the arc $L_k$ before the positional compensation to the distal end of the arc position compensation completed portion 67. That is, the arc $L_k$ is parallel translated from a position indicated by a dotted line in FIG. 11 to a position indicated by a solid line in FIG. 11. As a result, an arc boundary between the arc $L_{k-1}$ and the arc $L_k$ becomes continuous, and the position of the arc $L_k$ is compensated.

It is to be noted that a position of each arc $L_j$ other than the arc $L_k$ is also compensated by the arc position compensating section 53. That is, when performing the positional compensation of the arc $L_j$, the arc position compensating section 53 is configured to parallel translate the arc $L_j$ a distance from a proximal end of the arc $L_j$ before the positional compensation to the distal end (the end on the side far from the origin of the global coordinate system C) of the arc position compensation completed portion 67. As a result, an arc boundary between the arc $L_j$ and an arc $L_{j-1}$ adjacent to the proximal end side (the side close to the origin of the global coordinate system C) of the arc $L_j$ becomes continuous, and the position of the arc $L_j$ is compensated. However, in regard to an arc $L_1$, since a proximal end of the arc $L_1$ is the origin of the global coordinate system C, the positional compensation is not performed.

As shown in FIG. 4, when the curve interpolation of the detected linear form 61 by the curve form detecting section 50 is completed and the detected curve form 65 is formed, whether inspection by the endoscopic form detection device 1 has been completed is confirmed (a step S107). When the inspection has not been completed (the step S107—No), the processing returns to the step S101 to detect a form of the inserting section 11 of the endoscope 10 in the next stationary state. When the inspection has been completed (the step S107—Yes), the form detection of the inserting section 11 of the endoscope 10 is finished.

Therefore, the endoscopic form detection device 1 and the form detecting method of the inserting section 11 of the endoscope 10 using the endoscopic form detection device 1 exercise the following effect. That is, in the endoscopic form detection device 1, a posture detecting section 30 is configured to detect a posture of each sensor unit $S_i$ from measurement data of the sensor unit $S_i$, and the linear form detecting section 40 is configured to detect the detected linear form 61 of the inserting section 11 of the endoscope 10 from the posture of each sensor unit $S_i$. Furthermore, the curve form detecting section 50 is configured to carry out the curve interpolation of the detected linear form 61 to detect the detected linear form 65. As described above, since the detected linear form 65 of the inserting section 11 is detected from the measurement data of each sensor unit $S_i$ arranged in the inserting section 11 configured to be inserted in a body cavity at the time of observation, a sense coil and others do not have to be provided outside a body. Therefore, miniaturization and simplification of the endoscopic form detection device 1 can be realized.

Additionally, in the endoscopic form detection device 1, the curve form detecting section 50 is configured to perform the curve interpolation of the detected linear form 61 on the assumption that a form between the respective sensor units $S_i$ is the arc $L_j$ whose arc length is equal to the inter-sensor dimension l, and configured to detect the detected curve form 65. In fact, although there are differences among products, the inserting section 11 of the endoscope 10 has appropriate elasticity. Therefore, a curvature of the curved form of the inserting section 11 varies only slightly. Therefore, when the curve interpolation is performed on the assumption that a form between the sensor units $S_i$ is the arc $L_1$ having a radius $R_j$ (curvature $1/R_j$), it is possible to detect the detected curve form 65 having a small error from an actual curved form of the inserting section 11. As a result, the detected curve form 65 of the inserting section 11 can be highly accurately detected.

Further, in the endoscopic form detection device 1, an acceleration sensor $A_i$ is configured to measure gravitational acceleration and a geomagnetic sensor $B_i$ is configured to measure geomagnetism in the stationary state in which the inserting section 11 is not moving. Furthermore, the posture detecting section 30 is configured to detect a posture of each sensor unit $S_i$ from the measured gravitational acceleration and geomagnetism. In the stationary state, each of the gravitational acceleration and the geomagnetism constantly has a fixed intensity in a fixed direction. Since a posture of each sensor unit $S_i$ is detected from the gravitational acceleration and the geomagnetism, the posture of the sensor unit Si can be highly accurately detected even in the stationary state. As a result, the detected curve form 65 of the inserting section 11 can be highly accurately detected.

Second Embodiment

A second embodiment according to the present invention will now be described with reference to FIG. 12 to FIG. 15. It is to be noted that like reference numerals denote the same parts or parts having the same functions as those in the first embodiment, thereby omitting description thereof.

FIG. 12 is a view showing a configuration of a personal computer 8 according to this embodiment. As shown in FIG. 12, a personal computer 8 includes a communicating section 26, a physical quantity converting section 28, a posture detecting section 30, a linear form detecting section 40, a drawing section 45, and a display section 47 like the first embodiment. A curve form detecting section 70 is connected to the linear form detecting section 40 and the drawing section 45.

Like the curve form detecting section 50 according to the first embodiment, the curve form detecting section 70 is configured to perform curve interpolation with respect to a detected linear form 61 on the assumption that a form between respective sensor units $S_i$ is an arc $L_j$ (j=1, 2, ... N) whose arc length is equal to an inter-sensor dimension l, and configured to detect a detected curve form 81. However, a technique of detecting the detected curve form 81 is different from that of the curve form detecting section 50.

The curve form detecting section 70 includes an interpolation sequentially implementing section 71 as a curve interpolating section configured to sequentially perform curve interpolation in accordance with each link $T_j$ starting from a link $T_j$ on a proximal end side (a side close to an origin of a global coordinate system C) to form an arc $L_j$, and an interpolation controlling section 72 configured to control the interpolation sequentially implementing section 71 to carry out the curve interpolation with respect to all the links $T_j$. Further, the curve form detecting section 70 includes an uninterpolated link position compensating section 73 configured to parallel translate an interpolation uncompleted portion 85 constituted of a link that is not subjected to the curve interpolation (an uninterpolated link) $T_j$ to compensate a position every time the curve interpolation of one link $T_j$ is carried out by the interpolation sequentially implementing section 71. The interpolation uncompleted portion 85 is parallel translated by the uninterpolated link position compensating section 73 in such a manner that a boundary between the interpolation uncompleted portion 85 and an interpolation completed portion 83 constituted of an arc $L_j$ formed by the curve interpolation becomes continuous.

As shown in FIG. 12, the interpolation sequentially implementing section 71 includes a normal line forming section 75, a center deciding section 77, and an arc forming section 79. Details of the normal line forming section 75, the center deciding section 77, and the arc forming section 79 will be described later.

Here, description will now be given as to a method of using the curve form detecting section 70 to perform the curve interpolation of the detected linear form 61 detected by the linear form detecting section 40 and to thereby detect the detected curve form 81. Like the curve form detecting section 50 according to the first embodiment, the curve form detecting section 70 is configured to carry out the curve interpolation of the detected linear form 61 on the assumption that a form between the respective sensor units $S_i$ is the arc $L_j$ whose arc length is equal to the inter-sensor dimension l (a step S106 in FIG. 4). As a result, as described in the first embodiment, the detected curve form 81 having a small error from an actual curve form of the inserting section 11 is formed.

When performing the curve interpolation of the detected linear form 61, the interpolation sequentially implementing section 71 is configured to sequentially carry out the curve interpolation in accordance with each link $T_j$ starting from the link $T_j$ on the proximal end side (the side close to the origin of the global coordinate system C) to form the arc $L_j$. Here, a method of using the interpolation sequentially implementing section 71 to perform the curve interpolation of the link $T_j$ will now be described. Here, description will be given as to the curve interpolation of a kth link $T_k$ from the proximal end side between a kth sensor unit $S_{k-1}$ from the proximal end side and a (k+1)th sensor unit $S_k$ from the proximal end side.

FIG. 13 is a flowchart showing a method of detecting the detected curve form 81 from the detected linear form 61 by the curve form detecting section 70. FIG. 14 is a view explaining processing in the interpolation sequentially implementing section 71. As shown in FIG. 14, in a state before the curve interpolation of the link $T_k$ is carried out by the interpolation sequentially implementing section 71, the curve interpolation from a first link to a link $T_{k-1}$ has been completed, and an interpolation completed portion 83 is formed. The interpolation completed portion 83 is constituted of arcs $L_1$ to $L_{k-1}$. Further, an interpolation uncompleted portion 85 constituted of links (interpolation uncompleted links) $T_k$ to $T_N$ which have not been subjected to the interpolation is formed. At this time, a boundary between the interpolation completed portion 83 and the interpolation uncompleted portion 85 is continuous, and the sensor unit $S_k$ is placed at a point $U'_k$.

In this state, the interpolation sequentially implementing section 71 is configured to carry out the curve interpolation of the link (an interpolation target link) $T_k$ placed on the most proximal end side in the interpolation uncompleted portion 85. As shown in FIG. 13 and FIG. 14, when performing the curve interpolation of the link $T_k$, the normal line forming section 75 is configured to first form a first interpolation normal line $N_{k-1}$ that runs through a proximal end (a first end point) of the link $T_k$ and is perpendicular to the link $T_k$ and a second interpolation normal line $N_k$ that runs through a distal end (a second end point) of the link $T_k$ and is perpendicular to a link (an interpolation target adjacent link) $T_{k+1}$ adjacent to the distal end side of the link $T_k$ (a step S121).

Furthermore, the center deciding section 77 is configured to calculate an intersection $O_k$ of the first interpolation normal line $N_{k-1}$ and the second interpolation normal line $N_k$ and configured to decide the intersection $O_k$ as the center of an arc $L_k$ (a step S122). If the first interpolation normal line $N_{k-1}$ and the second interpolation normal line $N_k$ do not cross each other, an intermediate point $O_k$ of two points that minimize a distance between the first interpolation normal line $N_{k-1}$ and the second interpolation normal line $N_k$ is calculated. The intermediate point $O_k$ is calculated by the same technique as that in the first embodiment. Moreover, the intermediate point $O_k$ is determined as the center $O_k$ of the arc $L_k$ (a step S122).

Additionally, the arc forming section 79 is configured to form the arc $L_k$ (a step S123). The arc $L_k$ has a radius $R_k$ equal to a distance between the center $O_k$ decided by the center deciding section 77 and the proximal end of the link (the interpolation target link) $T_k$. That is, the arc $L_k$ has curvature $1/R_k$. Further, the arc $L_k$ is the arc $L_k$ whose arc length starting from the proximal end of the link $T_k$ is equal to the inter-sensor dimension l. A distal end $U_k$ of the arc $L_k$ is a position of the sensor unit $S_k$ after the curve interpolation. That is, the position of the sensor unit $S_k$ moves from the point $U'_k$ to the point $U_k$ by the curve interpolation of the link $T_k$. When the position of the sensor unit $S_k$ moves, the boundary between the interpolation completed portion 83 and the interpolation uncompleted portion 85, which was continuous in the state before the curve interpolation of the link $T_k$ was carried out by the interpolation sequentially implementing section 71, becomes discontinuous. That is, the arc $L_k$ and the link $T_{k+1}$ become discontinuous.

It is to be noted that the curve interpolation is likewise carried out with respect to each link $T_j$ other than the link $T_k$ by the interpolation sequentially implementing section 71. That is, when performing the curve interpolation of the link (an interpolation target link) $T_j$, the normal line forming section 75 is configured to form a first interpolation normal line $N_{j-1}$ that runs through a first end point which is a proximal end (an end on a side close to the origin of the global coordinate C) of the link $T_j$ and is perpendicular to the link $T_j$ and a second interpolation normal line $N_j$ that runs through a second end point which is a distal end (an end on a side far from the origin of the global coordinate C) of the link $T_j$ and is perpendicular to a link (an interpolation target adjacent link) $T_{j+1}$ adjacent to the distal end side (the side far from the origin of the global coordinate C) of the link $T_j$ (the step S121). Furthermore, the center deciding section 77 is configured to calculate an intersection $O_j$ of the first interpolation normal line $N_{j-1}$ and the second interpolation normal line $N_j$ or an intermediate point $O_j$ of two points that minimize a distance between the first interpolation normal line $N_{j-1}$ and the second interpolation normal line $N_j$ and configured to decide the intersection $O_j$ or the intermediate point $O_j$ as the center $O_j$ of an arc $L_j$ (the step S122). Moreover, the arc forming section 79 is configured to form the arc $L_j$ whose radius $R_j$ is equal to a distance between the center $O_j$ and the proximal end of the link (the interpolation target link) $T_j$ and whose arc length starting from the proximal end of the link $T_j$ is equal to the inter-sensor dimension l (the step S123).

FIG. 15 is a view explaining processing in the unimplemented link position compensating section 73. As shown in FIG. 15, a state after the curve interpolation of the link $T_k$ was carried out by the interpolation sequentially implementing section 71 to form the arc $L_k$, the interpolation completed portion 83 which has been completely subjected to the curve interpolation and the interpolation uncompleted portion 85 which has not been subjected to the curve interpolation are formed. The interpolation completed portion 83 is constituted of the arcs $L_1$ to $L_k$, and the interpolation uncompleted portion 85 is constituted of the links $T_{k+1}$ to $T_N$. At this time, since the position of the sensor unit $S_k$ is moved from the point $U'_k$ to the point $U_k$ by the curve interpolation of the link $T_k$ as described above, the boundary between the interpolation completed portion 83 and the interpolation uncompleted portion 85 is discontinuous. In this state, the uninterpolated link position compensating section 73 is configured to parallel translate the interpolation uncompleted portion 85 in such a manner that the boundary between the interpolation uncompleted portion 85 and the interpolation completed portion 83 becomes continuous to compensate the position of the interpolation uncompleted portion 85 (a step S124). That is, the interpolation uncompleted portion 85 is parallel translated from the position indicated by the dotted line in FIG. 15 to the position indicated by the solid line in FIG. 15.

It is to be noted that, in regard to each link $T_j$ other than the link $T_k$, a position of the interpolation uncompleted portion 85 is likewise compensated by the uninterpolated link position compensating section 73. That is, after the curve interpolation of the link $T_j$ is performed by the interpolation sequentially implementing section 71, the boundary between the interpolation completed portion 83 and the interpolation uncompleted portion 85 is discontinuous. In this state, the uninterpolated link position compensating section 73 is configured to parallel translate the interpolation uncompleted portion 85 to be continuous with the interpolation completed portion 83, thereby compensating the position of the interpolation uncompleted portion 85 (the step S124). The uninterpolated link position compensating section 73 is configured to compensate the position of the interpolation uncompleted portion 85 every time the curve interpolation of one link $T_j$ is carried out by the interpolation sequentially implementing section 71.

Furthermore, as shown in FIG. 13, the interpolation controlling section 72 is configured to confirm whether the curve interpolation has been completed with respect to all the links $T_1$ (a step S125). When the curve interpolation has been completed with respect to all the links $T_j$, the detected curve form 81 of the inserting section 11 is formed, and the processing advances to the next step (the step S125—Yes). When the curve interpolation has not been completed with respect to all the links $T_j$, the processing returns to the step S121 (the step S125—No), and the interpolation sequentially implementing section 71 performs the curve interpolation of the link (the interpolation target link) $T_j$ placed on the most proximal end side (the side close to the origin of the global coordinate system C) in the interpolation uncompleted portion 85. That is, the interpolation sequentially implementing section 71 is configured to be controlled in such a manner that the steps S121 to S123 are carried out until the curve interpolation is completed with respect to all the links $T_j$. Moreover, when the interpolation sequentially implementing section 71 performs the curve interpolation of the next link $T_j$ (the steps S121 to S123), the uninterpolated link position compensating section 73 is configured to compensate the position of the interpolation uncompleted portion 85 (the step S124).

Therefore, the endoscopic form detection device 1 and the form detecting method of the inserting section 11 of the endoscope 10 using the endoscopic form detection device 1 exercise the following effect. That is, in the endoscopic form detection device 1, the posture detecting section 30 is configured to detect a posture of each sensor unit $S_i$ from measurement data of each sensor unit $S_i$, and the linear form detecting section 40 is configured to detect the detected linear form 61 of the inserting section 11 of the endoscope 10 from the posture of each sensor unit $S_i$. Furthermore, the curve form detecting section 70 is configured to carry out the curve interpolation of the detected linear form 61 to detect the detected curve form 81. As described above, since the detected curve form 81 of the inserting section 11 is detected from the measurement data of each sensor unit $S_i$ arranged in the inserting section 11 configured to be inserted in a body cavity at the time of observation, a sense coil and others do not have to be provided outside a body. Therefore, miniaturization and simplification of the endoscopic form detection device 1 can be realized.

Additionally, in the endoscopic form detection device 1, the curve form detecting section 70 is configured to perform the curve interpolation of the detected linear form 61 on the assumption that a form between the respective sensor units $S_i$ is the arc $L_j$ whose arc length is equal to the inter-sensor dimension l, and configured to detect the detected curve form 81. In fact, although there are differences among products, the inserting section 11 of the endoscope 10 has appropriate elasticity. Therefore, curvature of the curved form of the inserting section 11 varies only slightly. Therefore, when the curve interpolation is performed on the assumption that a form between the sensor units $S_i$ is the arc $L_j$ having a radius $R_j$ (curvature $1/R_j$), it is possible to detect the detected curve form 81 having a small error from an actual curved form of the inserting section 11. As a result, the detected curve form 81 of the inserting section 11 can be highly accurately detected.

Further, in the endoscopic form detection device 1, an acceleration sensor $A_i$ is configured to measure gravitational acceleration and a geomagnetic sensor $B_i$ is configured to measure geomagnetism in the stationary state in which the inserting section 11 is not moving. Furthermore, the posture detecting section 30 is configured to detect a posture of each sensor unit $S_i$ from the measured gravitational acceleration and geomagnetism. In the stationary state, each of the gravitational acceleration and the geomagnetism constantly has a fixed intensity in a fixed direction. Since a posture of each sensor unit $S_i$ is detected from the gravitational acceleration and the geomagnetism, the posture of the sensor unit $S_i$ can be highly accurately detected even in the stationary state. As a result, the detected curve form 81 of the inserting section 11 can be highly accurately detected.

(First Modification)

A first modification of the foregoing embodiment will now be described with reference to FIG. 16 and FIG. 17. It is to be noted that like reference numerals denote the same parts and parts having the same functions as those in the first embodiment and the second embodiment, thereby omitting description thereof.

In this modification, a form of an inserting section 11 can be detected in a moving state in which the inserting section 11 of an endoscope 10 is being parallel translated. The detection of the form of the inserting section 11 in the moving state is carried out between the step S106 and the step S107 in FIG. 4. FIG. 16 is a view showing a configuration of a personal computer 8 according to this modification. FIG. 17 is a flowchart showing a technique of detecting the form of the inserting section 11 in the moving state.

As shown in FIG. 16, like the first embodiment, the personal computer 8 includes a communicating section 26, a physical quantity converting section 28, a posture detecting section 30, a linear form detecting section 40, a drawing section 45, a display section 47, and a curve form detecting section 50.

An acceleration detecting section 90 is connected to the physical quantity converting section 28. As shown in FIG. 17, when detecting a form of the inserting section 11 in the moving state, the acceleration detecting section 90 is configured to acquire acceleration data in the moving state measured by an acceleration sensor $A_i$ of each sensor unit $S_i$ (a step S131). Further, the acceleration detecting section 90 is configured to divide an acceleration vector measured at the center of each sensor unit Si into an X axis directions component, a Y axis directions component, and a Z axis directions component of a global coordinate system C based on the acceleration data in the moving state. Further, the X axis directions component, the Y axis directions component, and the Z axis directions component of the global coordinate system C of the acceleration vector measured at the center of each sensor unit $S_i$ are detected (a step S132).

Here, description will now be given as to a technique of detecting the X axis directions component, the Y axis directions component, and the Z axis directions component in the global coordinate system C of the acceleration vector measured at the center of each sensor unit Si by the acceleration detecting section 90. In the moving state, since components produced due to movement of the inserting section 11 are added to gravitational acceleration generated in the vertical directions in the stationary state, the X axis directions component, the Y axis directions component, and the Z axis directions component in the global coordinate system C of the acceleration vector measured at the center of each sensor unit $S_i$ are represented as follows:

$$\dot{a}_{thi} = [a_{thi\_X}\ a_{thi\_Y} - g + a_{thi\_Z}]^T \quad (17)$$

Moreover, an $X_i$ axis directions component, a $Y_i$ axis directions component, and a $Z_i$ axis directions component in a local coordinate system $C_i$ of an acceleration vector measured by the acceleration sensor $A_i$ of each sensor unit $S_i$ are represented as follows:

$$\dot{a}_{obsi}' = [a_{Bi\_X}'\ a_{Bi\_Y}'\ a_{Bi\_Z}']^T \quad (18)$$

Additionally, in this modification, since a situation where the inserting section 11 of the endoscope 10 is being parallel translated is considered, it is assumed that the sensor units arranged in proximity to each other have the same acceleration vector in the global coordinate system C. In the actual endoscope 10, since the inter-sensor dimension l between the respective sensor units $S_i$ is very small, such an assumption is possible. When the assumption is set in this manner, the following relationship is achieved between, e.g., an acceleration vector measured by a sensor unit $S_1$ and acceleration vector measured by a sensor unit $S_2$:

$$\dot{a}_{th1} = \dot{a}_{th2} \quad (19.1)$$

$$\|\dot{a}_{obs1}'\| = \|\dot{a}_{obs2}'\| \quad (19.2)$$

Additionally, based on Expression (19.1) and Expression (19.2), the following relationship can be achieved:

$$[a_{th1\_X}\ a_{th1\_Y}\ a_{th1\_Z}]^T = [a_{th2\_X}\ a_{th2\_Y}\ a_{th2\_Z}]^T \quad (20.1)$$

$$[a_{B1\_X}'\ a_{B1\_Y}'\ a_{B1\_Z}']^T = \\ \left[a_{B2\_X}'\ a_{B2\_Y}'\ \sqrt{\|\dot{a}_{obs1}'\|^2 - (a_{B2\_X}'^2 + a_{B2\_Y}'^2)}\right]^T \quad (20.2)$$

Here, in the sensor unit $S_1$, based on a relationship between the global coordinate system C and the local coordinate system $C_1$, the following expression can be attained by using a rotation matrix in Expression (1):

$$\dot{a}'_{obs1} = (C^G_{B1})^T \dot{a}_{th1} = \begin{bmatrix} -\sin\gamma_1 \cdot \sin\alpha_1 \cdot \sin\beta_1 + \cos\beta_1 \cdot \cos\gamma_1 & -\sin\gamma_1 \cdot \cos\alpha_1 & \sin\gamma_1 \cdot \sin\alpha_1 \cdot \cos\beta_1 + \sin\beta_1 \cdot \cos\gamma_1 \\ \cos\gamma_1 \cdot \sin\alpha_1 \cdot \sin\beta_1 + \cos\beta_1 \cdot \sin\gamma_1 & \cos\gamma_1 \cdot \cos\alpha_1 & -\cos\gamma_1 \cdot \sin\alpha_1 \cdot \cos\beta_1 + \sin\beta_1 \cdot \sin\gamma_1 \\ -\cos\alpha_1 \cdot \sin\beta_1 & \sin\alpha_1 & \cos\alpha_1 \cdot \cos\beta_1 \end{bmatrix} \quad (21)$$

$$\begin{bmatrix} a_{th1\_X} \\ a_{th1\_Y} \\ -g + a_{th1\_Z} \end{bmatrix}$$

Likewise, in the sensor unit $S_2$, based on a relationship between the global coordinate system C and a local coordinate system $O_2$, the following expression can be achieved by using the rotation matrix in Expression (1):

$$\dot{a}'_{obs2} = (C^G_{B2})^T \dot{a}_{th2} = \begin{bmatrix} -\sin\gamma_2 \cdot \sin\alpha_2 \cdot \sin\beta_2 + \cos\beta_2 \cdot \cos\gamma_2 & -\sin\gamma_2 \cdot \cos\alpha_2 & \sin\gamma_2 \cdot \sin\alpha_2 \cdot \cos\beta_2 + \sin\beta_2 \cdot \cos\gamma_2 \\ \cos\gamma_2 \cdot \sin\alpha_2 \cdot \sin\beta_2 + \cos\beta_2 \cdot \sin\gamma_2 & \cos\gamma_2 \cdot \cos\alpha_2 & -\cos\gamma_2 \cdot \sin\alpha_2 \cdot \cos\beta_2 + \sin\beta_2 \cdot \sin\gamma_2 \\ -\cos\alpha_2 \cdot \sin\beta_2 & \sin\alpha_2 & \cos\alpha_2 \cdot \cos\beta_2 \end{bmatrix} \quad (22)$$

$$\begin{bmatrix} a_{th2\_X} \\ a_{th2\_Y} \\ -g + a_{th2\_Z} \end{bmatrix}$$

When Expression (21) and (22) are solved by utilizing the relationship represented by Expression (20.1), an X axis directions component $a_{th1\_X}(a_{th2\_X})$, a Y axis directions component $a_{th1\_Y}(a_{th2\_Y})$, and a Z axis directions component $a_{th1\_Z}(a_{th2\_Z})$ in the global coordinate system C of the acceleration vector other than the gravitational acceleration measured in the sensor unit $S_1$ or $S_2$ can be obtained. When the rotation matrix in Expression (1) is used, a relationship between the respective axis directions components in the global coordinate system C of a geomagnetic vector measured by a geomagnetic sensor $B_i$ represented by Expression (13) and respective axis directions components in the local coordinate system $C_i$ of a geomagnetic vector represented by Expression (9) is as follows:

$$\dot{M}_{obsi} = (C^G_{Bi})^T \dot{M}_{th} = \begin{bmatrix} -\sin\gamma_i \cdot \sin\alpha_i \cdot \sin\beta_i + \cos\beta_i \cdot \cos\gamma_i & -\sin\gamma_i \cdot \cos\alpha_i & \sin\gamma_i \cdot \sin\alpha_i \cdot \cos\beta_i + \sin\beta_i \cdot \cos\gamma_i \\ \cos\gamma_i \cdot \sin\alpha_i \cdot \sin\beta_i + \cos\beta_i \cdot \sin\gamma_i & \cos\gamma_i \cdot \cos\alpha_i & -\cos\gamma_i \cdot \sin\alpha_i \cdot \cos\beta_i + \sin\beta_i \cdot \sin\gamma_i \\ -\cos\alpha_i \cdot \sin\beta_i & \sin\alpha_i & \cos\alpha_i \cdot \cos\beta_i \end{bmatrix} \quad (23)$$

$$\begin{bmatrix} E_X \\ E_Y \\ E_Z \end{bmatrix}$$

When solving Expressions (20.1), (21), and (22) including the relational expression of the geomagnetism obtained by i=1 (or 2) assigned in Expression (23), a total of 12 unknowns, i.e., six posture angles and six accelerations are present with respect to 12 equations. As a result, it is possible to mathematically solve the X axis directions component $a_{th1\_X}(a_{th2\_X})$, the Y axis directions component $a_{th1\_Y}(a_{th2\_Y})$, and the Z axis directions component $a_{th1\_Z}(a_{th2\_Z})$ in the global coordinate system C of the acceleration vector other than the gravitational acceleration measured by each of the sensor unit $S_1$ and $S_2$. In regard to any other sensor unit $S_i$, likewise, an X axis directions component $a_{thi\_X}$, a Y axis directions component $a_{thi\_Y}$, and a Z axis directions component $a_{thi\_Z}$ in the global coordinate system C of an acceleration vector other than the gravitational acceleration measured by each sensor unit $S_i$ can be obtained.

A displacement calculating section 92 is connected to the acceleration detecting section 90. The displacement calculating section 92 is configured to calculate a displacement of each sensor unit $S_i$ from the previous stationary state based on the acceleration vector other than the gravitational acceleration detected by the acceleration detecting section 90 (a step S133). An X axis directions component, a Y axis directions component, and a Z axis directions component in the global coordinate system C of the displacement of each sensor unit $S_i$ from the previous stationary state can be obtained by performing double integration with respect to the X axis directions component $a_{thi\_X}$, the Y axis directions component $a_{thi\_Y}$, and the Z axis directions component $a_{thi\_Z}$ in the global coordinate system C of the acceleration vector other than the gravitational acceleration measured by each sensor unit $S_i$. Additionally, the displacement calculating section 92 also is configured to calculate an X axis directions component, a Y axis directions component, and a Z axis directions component in the global coordinate system C of a velocity vector of each sensor unit $S_i$. The X axis directions component, the Y axis directions component, and the Z axis directions component in the global coordinate system C of the velocity vector of each sensor unit $S_i$ can be obtained by performing integration only once with respect to the X axis directions component $a_{thi\_X}$, the Y axis directions component $a_{thi\_Y}$, and the Z axis directions component $a_{thi\_Z}$ in the global coordinate system C of the acceleration vector other than the gravitational acceleration measured by each sensor unit $S_i$.

A movement state detecting section 94 is connected to the displacement calculating section 92. The movement state detecting section 94 is connected to the curve form detecting section 50. As shown in FIG. 17, when detecting a form of the inserting section 11 in the moving state, a detected curve form 65 of the inserting section 11 in the previous stationary state is detected by the above-described technique (the steps S101 to S106 in FIG. 4). The detected curve form 65 of the inserting section 11 in the previous stationary state is input to the movement state detecting section 94 from the curve form detecting section 50. Furthermore, a calculation result of the X axis directions component, the Y axis directions component, and the Z axis directions component in the global coordinate system C of displacement of each sensor unit $S_i$ from the previous stationary state is input to the movement state detecting section 94 from the displacement calculating section 92. The movement state detecting section 94 is configured to detect a movement state of the inserting section 11 from the previous stationary state based on the detected curve form 65 of the inserting section 11 in the previous stationary state and the displacement of each sensor unit $S_i$ from the previous stationary state (a step S134). As a result, a form of the inserting section 11 of the endoscope 10 in the moving state is detected.

The drawing section 45 is connected to the movement state detecting section 94. The detected form of the inserting section 11 in the moving state in the global coordinate system C detected by the movement state detecting section 94 is drawn by the drawing section 45. An operator can confirm the detected form in the moving state drawn by the drawing section 45 in the display section 47.

Additionally, a staying state detecting section 96 is connected to the displacement calculating section 92. A warning section 97 is connected to the staying state detecting section 96. The staying state detecting section 96 is configured to detect a staying state of the inserting section 11 based on X axis directions components, Y axis directions components, and Z axis directions components in the global coordinate system C of the acceleration vector, the velocity vector, and the displacement of each sensor unit $S_i$ (a step S135). That is, when observing, e.g., a sigmoid colon by using the endoscope 10, a state in which the inserting section 11 is staying at an S-top and the like is detected. As a result, an operator can confirm whether an operation in the operating section 12 has been transmitted to the inserting section 11. When the inserting section 11 is staying (the step S135—Yes), the warning section 98 is configured to carry out warning display (a step S136). When the inserting section 11 is not staying (the step S135—No), the warning display is not performed, and the processing advances to a step S107 (see FIG. 4).

As described above, in the endoscopic form detection device 1 according to this modification, the X axis directions component, the Y axis directions component, and the Z axis directions component in the global coordinate system C of the acceleration vector measured at the center of each sensor unit $S_i$ by the acceleration detecting section 90 are detected. Further, the displacement calculating section 92 also is configured to calculate the X axis directions components, the Y axis directions components, and the Z axis directions components in the global coordinate system C of the displacement and the velocity vector of each sensor unit $S_i$. Based on the calculated acceleration vector, velocity vector, displacement, and the detected form 65 in the previous stationary state, the movement state detecting section 94 is configured to detect the form of the inserting section 11 in the moving state. Furthermore, based on the calculated acceleration vector, velocity vector, and displacement, the staying state detecting section 96 is configured to detect the staying state of the inserting section 11. Moreover, when the staying state is detected, the warning section 98 is configured to perform the warning display. With such a configuration, an operator can confirm whether an operation in the operating section 12 has been transmitted to the inserting section 11. As a result, when operating the endoscope 10, the operator can make a more appropriate judgment.

(Other Modifications)

It is to be noted that the curve compensating section 51 is configured to first perform the curve interpolation with respect to all the links $T_j$ to form the arcs $L_j$ in the first embodiment. Further, the arc position compensating section 53 is configured to parallel translate each arc $L_j$ in such a manner that the boundaries between the arc $L_j$ and the adjacent arcs $L_{j-1}$ and $L_{j+1}$ become continuous, thereby compensating the position of the arc $L_j$. On the other hand, in the second embodiment, the interpolation sequentially implementing section 71 is configured to sequentially carry out the curve interpolation starting from the link $T_j$ on the proximal end side in accordance with each link $T_j$. Furthermore, the interpolation uncompleted portion 85 is parallel translated to be continuous with the interpolation completed portion 83 every time the curve interpolation is effected with respect to one link $T_j$, thereby compensating the position of the interpolation uncompleted portion 85. That is, the detected curve form 65 detected by the curve form detecting section 70 in the first embodiment is equal to the detected curve form 81 detected by the curve form detecting section 70 in the second embodiment. Based on the above configuration, the circuit architecture and others are complicated, but the present invention may include a curve form detecting section which is a combination of the first embodiment and the second embodiment. For example, this curve form detecting section is configured to first carry out the curve interpolation from the first link to a link $T_k$ to form arcs $L_1$ to $L_k$ like the first embodiment and then configured to perform the positional compensation of the arcs $L_1$ to $L_k$. Furthermore, in regard to a link $T_{k+1}$ and subsequent links, the positional compensation of the interpolation uncompleted portion 85 is effected every time the curve interpolation of one link $T_j$ is carried out like the second embodiment.

Moreover, in the foregoing embodiments, each local coordinate system $C_i$ is a coordinate system whose $Y_i$ axis directions coincide with the longitudinal directions at the center of the sensor unit $S_i$. However, in the present invention, each local coordinate system $C_i$ can suffice as long as an origin is set at the center of the sensor unit $S_i$ and axial directions of any one of an $X_i$ axis, a $Y_i$ axis, and a $Z_i$ axis coincide with the longitudinal directions at the center of the sensor unit $S_i$. However, when the $X_i$ axis is the longitudinal axis, the following equation is used in place of $e_{yk-1}$ in Expression (16.1) and Expression (16.2):

$$e_{xk-1} = [1\ 0\ 0]^T \quad (24)$$

Likewise, when the $Z_i$ axis is the longitudinal axis, the following equation is used in place of $e_{yk-1}$ in Expression (16.1) and Expression (16.2):

$$e_{zk-1} = [0\ 0\ 1]^T \quad (25)$$

Here, $e_{xk-1}$ is a unit vector in $X_{k-1}$ axis directions which are the longitudinal directions at the origin in a local coordinate system $C_{k-1}$, and $e_{zk-1}$ is a unit vector in $Z_{k-1}$ axis directions which are the longitudinal directions at the origin of the local coordinate system $C_{k-1}$.

Furthermore, in the foregoing embodiments, the global coordinate system C is a coordinate system in which an origin is set at the center of the sensor unit $S_0$ provided on the most proximal end side, a Z axis coincides with the vertical directions, and an X axis and a Y axis are arranged on a horizontal plane. However, in the present invention, any coordinate system can suffice as long as any one of an X axis, a Y axis, and a Z axis is a vertical axis whose axial directions coincide with the vertical directions and two axes other than the vertical axis are horizontal axes arranged on the horizontal plane. As a result, the posture detecting section 30 can detect a posture of each sensor unit $S_i$ based on gravitational acceleration measured by the acceleration sensor $A_i$ and geomagnetism measured by the geomagnetic sensor $B_i$. However, when the X axis is the vertical axis, each of an X axis directions component, a Y axis directions component, and a Z axis directions component in the global coordinate system C of a gravitational acceleration vector represented by Expression (2) is as follows:

$$\dot{a}_{th} = [-g\ 0\ 0]^T \quad (26)$$

In this case, although the posture angles $\alpha_i$, $\beta_i$, and $\gamma_i$ are the (Z, X, Y) type by which rotation is effected in the order of the yaw angle $\gamma_i$, the pitch angle $\alpha_i$, and the roll angle $\beta_i$ in the first embodiment, the rotation order of the posture angles $\alpha_i$, $\beta_i$, and $\gamma_i$ is changed and a rotation matrix different from that in Expression (1) is used. As a result, a first angle calculating section 34 is configured to calculate the posture angles $\beta_i$ and $\gamma_i$ about the Y axis and the Z axis which are the horizontal axes based on acceleration data measured by the acceleration sensor $A_i$. Further, a second angle calculating section 36 is configured to calculate the posture angle $\alpha_i$ about the X axis which is the vertical axis based on geomagnetic data measured by the geomagnetic sensor $B_i$. This configuration is likewise applied when the Y axis is the vertical axis, and the first angle calculating section 34 is configured to calculate the posture angles $\alpha_i$ and $\gamma_i$ about the X axis and the Z axis as the horizontal axes based on the acceleration data measured by the acceleration sensor $A_i$. Furthermore, the second angle calculating section 36 is configured to calculate the posture angle $\beta_i$ on the Y axis which is the vertical axis based on the geomagnetic data measured by the geomagnetic sensor $B_i$.

Moreover, although the global coordinate system C has the origin set at the center of the sensor unit $S_0$ provided on the most proximal end side in the foregoing embodiments, it may have the origin at the center of the sensor unit $S_N$ provided on the most distal end side. In this case, a link forming section 41 uses Expression (16.1) and Expression (16.2) to obtain a coordinate $P'_j$ ($l_{xj}$, $l_{yj}$, $l_{zj}$) of a sensor unit $S_{j-1}$ on a proximal end side (a side far from the origin of the global coordinate system C) of a link $T_j$ when a sensor unit $S_j$ on a distal end side (a side close to the origin of the global coordinate system C) of the link $T_j$ is placed at the origin of the global coordinate system C. Additionally, the link $T_j$ is formed by linearly connecting the origin of the global coordinate system C with the coordinate $P'_j$ ($l_{xj}$, $l_{yj}$, $l_{zj}$).

Further, in this case, when performing the curve interpolation with respect to the link (an interpolation target link) $T_j$ by the curve interpolating section 51 of the curve form detecting section 50, the normal line forming section 55 is configured to first form a first interpolation normal line $N_j$ that runs through a first end point as a distal end (an end on the side close to the origin of the global coordinate C) of the link $T_j$ and is perpendicular to the link $T_j$ and a second interpolation normal line $N_{j-1}$ that runs through a second end point as a proximal end (an end on the side far from the origin of the global coordinate C) of the link $T_j$ and is perpendicular to a link (an interpolation target adjacent link) $T_{j-1}$ adjacent to the proximal end side (the side far from the origin of the global coordinate C) of the link $T_j$. Furthermore, the center deciding section 57 is configured to calculate an intersection $O_j$ of the first interpolation normal line $N_j$ and the second interpolation normal line $N_{j-1}$ or an intermediate point $O_j$ of two points that minimize a distance between the first interpolation normal line $N_j$ and the second interpolation normal line $N_{j-1}$, and configured to decide the intersection $O_j$ or the intermediate point $O_j$ as the center $O_j$ of an arc $L_j$. Moreover, the arc forming section 59 is configured to form an arc $L_j$ whose radius $R_j$ is equal to a distance between the center $O_j$ and the distal end of the link (the interpolation target link) $T_j$ and whose arc length starting from the distal end of the link $T_j$ is equal to an inter-sensor dimension l.

Additionally, in this case, the interpolation sequentially implementing section 71 of the curve form detecting section 70 is configured to sequentially perform the curve interpolation from the link $T_j$ on the distal end side (the side close to the origin of the global coordinate system C) in accordance with each link $T_j$, thereby forming the arc $L_j$.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic form detection device comprising:
   an endoscope including an inserting section in which sensor units are arranged in longitudinal directions at intervals of a predetermined inter-sensor dimension;
   a posture detecting section configured to detect a posture of each of the sensor units based on measurement data in the sensor unit;
   a linear form detecting section configured to detect a detected linear form of the inserting section of the endoscope on an assumption that a form between the respective sensor units is a linear link whose dimension is equal to the inter-sensor dimension based on the posture of each of the sensor units detected by the posture detecting section; and
   a curve form detecting section configured to perform curve interpolation with respect to the detected linear form detected by the linear form detecting section on an assumption that a form between the respective sensor units is an arc whose arc length is equal to the inter-sensor dimension, and configured to detect a detected curve form, wherein
   the curve form detecting section includes:
   a curve interpolating section configured to carry out the curve interpolation in accordance with each of the links to form the arc between the respective sensor units; and
   an interpolation controlling section configured to control the curve interpolating section to perform the curve interpolation with respect to all the links, wherein
   the curve interpolating section includes:
   a normal line forming section configured to form, in a global coordinate system having
   an origin set at the center of the sensor unit provided on the most proximal end side or the most distal end side, a first interpolation normal line that runs through a first end point as an end on a side close to the origin in the global coordinate of an interpolation target link which is the link as a target of the curve interpolation performed by the curve interpolating section and that is perpendicular to the interpolation target link, and a second interpolation normal line that runs through a second end point as an end on a side far from the origin in the global coordinate of the interpolation target link and that is perpendicular to an interpolation target adjacent link which is the link adjacent to the side far from the origin in the global coordinate of the interpolation target link;

a center deciding section configured to calculate an intersection of the first interpolation normal line and the second interpolation normal line formed by the normal line forming section or an intermediate point of two points that minimize a distance between the first interpolation normal line and the second interpolation normal line, and configured to decide the intersection or the intermediate point as the center of the arc; and an arc forming section configured to form the arc which has a radius equal to a distance between the center and the first end point of the interpolation target link and a starting point at the first end point of the interpolation target link.

2. The device according to claim 1, wherein
the curve form detecting section includes an arc position compensating section configured to parallel translate each arc formed by the curve interpolating section in such a manner that an arc boundary between the arc and the adjacent arc becomes continuous, thereby being configured to compensate a position of the arc.

3. The device according to claim 1, wherein
the curve interpolating section is an interpolation sequentially implementing section configured to sequentially perform the curve interpolation, in a global coordinate system having an origin set at the center of the sensor unit provided on the most proximal end side or the most distal end side, starting from the link on a side close to the origin of the global coordinate system to form the arc, and the curve form detecting section includes an uninterpolated link position compensating section configured to parallel translate an interpolation uncompleted portion constituted of an uninterpolated link as the link which has not been subjected to the curve interpolation in such a manner that a boundary between the interpolation uncompleted portion and an interpolation completed portion constituted of the arc formed by the curve interpolation becomes continuous to thereby compensate a position of the interpolation uncompleted portion every time the curve interpolation of one link is carried out by the interpolation sequentially implementing section.

4. The device according to claim 1,
wherein each sensor unit includes:
an acceleration sensor configured to measure, in a local coordinate system in which an origin is set at the center of the sensor unit and any one of an X axis, a Y axis, and a Z axis is a longitudinal axis whose axial directions coincide with the longitudinal directions of the endoscope at the center of the sensor unit, three axis directions components of acceleration at the origin of the local coordinate system; and
a geomagnetic sensor configured to measure three axis directions components of geomagnetism at the origin of the local coordinate system in the local coordinate system.

5. The device according to claim 4,
wherein the posture detecting section includes a posture angle calculating section configured to calculate three posture angles, which are rotational angles about a vertical axis and horizontal axes in the local coordinate system of each sensor unit, with reference to a global coordinate system in which an origin is set at the center of the sensor unit provided on the most proximal end side or the most distal end side, any one of an X axis, a Y axis, and a Z axis is the vertical axis whose axial directions coincide with a vertical directions, and two axes other than the vertical axis are the horizontal axes arranged on a horizontal plane.

6. The device according to claim 5,
wherein the posture angle calculating section includes:
a first angle calculating section configured to calculate the two posture angles about the horizontal axes in the local coordinate system of each sensor unit from the global coordinate system based on acceleration data measured by the acceleration sensor; and
a second angle calculating section configured to calculate the posture angle about the vertical axis in the local coordinate system of each sensor unit from the global coordinate system based on geomagnetic data measured by the geomagnetic sensor.

7. A form detecting method of an inserting section of an endoscope, comprising:
performing measurement by using sensor units arranged in the inserting section of the endoscope in longitudinal directions at intervals of a predetermined inter-sensor dimension;
detecting a posture of each sensor unit by using a posture detecting section based on measurement data in the sensor unit;
detecting a detected linear form of the inserting section of the endoscope by using a linear form detecting section on the assumption that a form between the respective sensor units is a linear link whose dimension is equal to the inter-sensor dimension based on the posture of each sensor unit detected by the posture detecting section; and
performing curve interpolation with respect to the detected linear form detected by the linear form detecting section and forming a detected curve form by using a curve form detecting section on the assumption that a form between the respective sensor units is an arc whose arc length is equal to the inter-sensor dimension, wherein
the performing the curve interpolation with respect to the detected linear form and forming the detected curve form by the curve form detecting section includes:
performing the curve interpolation in accordance with each of the links and forming the arc between the respective sensor units by using a curve interpolating section of the curve form detecting section; and
controlling in such a manner that the curve interpolation is performed with respect to all the links by the curve interpolating section by using an interpolation controlling section of the curve form detecting section, wherein
the performing the curve interpolation in accordance with each of the links by the curve interpolating section includes:
forming, in a global coordinate system having an origin set at the center of the sensor unit provided on the most proximal end side or the most distal end side, a first interpolation normal line that runs through a first end point as an end on a side close to the origin in the global coordinate of an interpolation target link which is the link as a target of the curve interpolation performed by the curve interpolating section and that is perpendicular to the interpolation target link, and a second interpolation normal line that runs through a second end point as an end on a side far from the origin in the global coordinate of the interpolation target link and that is perpendicular to an interpolation target adjacent link which is the link adjacent to the side far from the origin in the global coordinate of the interpolation target link by using a normal line forming section of the curve interpolating section;

calculating an intersection of the first interpolation normal line and the second interpolation normal line formed by the normal line forming section or an intermediate point of two points that minimize a distance between the first interpolation normal line and the second interpolation normal line, and deciding the intersection or the intermediate point as the center of the arc by using a center deciding section of the curve interpolating section; and forming the arc which has a radius equal to a distance between the center and the first end point of the interpolation target link and a starting point at the first end point of the interpolation target link by using an arc forming section of the curve interpolating section.

8. The method according to claim 7, wherein
the performing the curve interpolation with respect to the detected linear form and forming the detected curve form by the curve form detecting section includes parallel translating each arc formed by performing the curve interpolation in accordance with each link with the use of the curve interpolating section in such a manner that an arc boundary between the arc and the adjacent arc becomes continuous, thereby compensating a position of the arc by using an arc position compensating section of the curve form detecting section.

9. The method according to claim 7, wherein
the performing the curve interpolation in accordance with each of the links by the curve interpolating section includes sequentially performing the curve interpolation, in a global coordinate system having an origin set at the center of the sensor unit provided on the most proximal end side or the most distal end side, stating from the link on a side close to the origin in the global coordinate system and forming the arc by using an interpolation sequentially implementing section serving as the curve interpolating section, and the performing the curve interpolation with respect to the detected linear form by the curve form detecting section to form a detected curve form includes parallel translating an interpolation uncompleted portion constituted of an uninterpolated link as the link which has not been subjected to the curve interpolation in such a manner that a boundary between the interpolation uncompleted portion and an interpolation completed portion constituted of the arc formed by the curve interpolation becomes continuous to thereby compensate a position of the interpolation uncompleted portion by using an interpolated link position compensating section of the curve form detecting section every time the curve interpolation of one link is carried out by the interpolation sequentially implementing section.

10. The method according to claim 7,
wherein the performing measurement in each of the sensor units includes:

measuring, in a local coordinate system in which an origin is set at the center of the sensor unit and any one of an X axis, a Y axis, and a Z axis is a longitudinal axis whose axial directions coincide with the longitudinal directions of the endoscope at the center of the sensor unit, three axis directions components of acceleration at the origin by using an acceleration sensor provided in each sensor unit; and measuring three axis directions components of geomagnetism at the origin in the local coordinate system by using a geomagnetic sensor provided in each sensor unit.

11. The method according to claim 10,
wherein the detecting a posture of each sensor unit by the posture detecting section includes calculating three posture angles, which are rotational angles about a vertical axis and horizontal axes in the local coordinate system of each sensor unit, with reference to a global coordinate system in which an origin is set at the center of the sensor unit provided on the most proximal end side or the most distal end side, any one of an X axis, a Y axis, and a Z axis is the vertical axis whose axial directions coincide with the vertical directions, and two axes other than the vertical axis are the horizontal axes arranged on a horizontal plane, by using a posture angle calculating section of the posture detecting section.

12. The method according to claim 11,
wherein the calculating the three posture angles about the vertical axis and the horizontal axes by the posture angle calculating section includes:

calculating the two posture angles about the horizontal axes in the local coordinate system of each sensor unit from the global coordinate system based on acceleration data measured by the acceleration sensor by using a first angle calculating section of the posture angle calculating section; and calculating the posture angle about the vertical axis in the local coordinate system of each sensor unit from the global coordinate system based on geomagnetic data measured by the geomagnetic sensor by using a second angle calculating section of the posture angle calculating section.

* * * * *